(12) United States Patent
Bettenga et al.

(10) Patent No.: US 11,350,952 B2
(45) Date of Patent: Jun. 7, 2022

(54) OPEN LATARJET FOR CORRECTION OF ANTERIOR-INFERIOR GLENOID BONE LOSS

(71) Applicant: Smith & Nephew, Inc., Memphis, TN (US)

(72) Inventors: Mason J. Bettenga, Memphis, TN (US); Stephen A. Santangelo, Sturbridge, MA (US); Nikhil N. Verma, Chicago, IL (US); Jeffrey Wyman, Naples, FL (US)

(73) Assignee: Smith & Nephew, Inc., Memphis, TN (US)

( * ) Notice: Subject to any disclaimer, the term of this patent is extended or adjusted under 35 U.S.C. 154(b) by 168 days.

(21) Appl. No.: 17/004,455

(22) Filed: Aug. 27, 2020

(65) Prior Publication Data
US 2020/0390453 A1 Dec. 17, 2020

Related U.S. Application Data

(62) Division of application No. 15/555,223, filed as application No. PCT/US2016/021705 on Mar. 10, 2016, now Pat. No. 10,806,472.
(Continued)

(51) Int. Cl.
*A61B 17/17* (2006.01)
*A61F 2/46* (2006.01)
(Continued)

(52) U.S. Cl.
CPC ........ *A61B 17/1778* (2016.11); *A61B 5/1076* (2013.01); *A61B 17/1684* (2013.01);
(Continued)

(58) Field of Classification Search
CPC ............ A61B 17/1796; A61B 17/8866; A61B 17/1684; A61B 17/2816; A61B 17/282;
(Continued)

(56) References Cited

U.S. PATENT DOCUMENTS

| | | | |
|---|---|---|---|
| 10,327,789 B2* | 6/2019 | Bouduban | A61B 17/1778 |
| 2009/0318923 A1* | 12/2009 | Burkhart | A61F 2/30734 |
| | | | 606/87 |

(Continued)

OTHER PUBLICATIONS

Office action received in corresponding Chinese application No. 201680014663.6 dated Nov. 5, 2020.

*Primary Examiner* — Marcela I. Shirsat
(74) *Attorney, Agent, or Firm* — Burns & Levinson LLP; Joseph Maraia; Marlo Grolnic

(57) ABSTRACT

Embodiments of the present disclosure are directed to instrumentation that facilitate coracoid-glenoid fixation in Latarjet procedures. For example, a single instrument, a coracoid resection tool, may be provided/utilized to prepare a coracoid bone graft for size, flatness, and hole drilling. A glenoid drill guide may further be provided/utilized that uses sized offsets for placement of the coracoid graft flush with the glenoid. Further embodiments of the disclosure are directed to corresponding methods that employ this instrumentation. For example, a surgeon may employs the coracoid resection tool as a guide to plane the inferior coracoid surface that will serve as the coracoid graft surface. The coracoid resection tool may further guide the placement of coracoid holes along the length of the coracoid and orient the holes approximately perpendicular to the planed coracoid graft surface. For example a proximal coracoid hole may be positioned towards the proximal end (i.e., the cut end) of the resected coracoid while a distal coracoid hole may be positioned towards the distal end (i.e., the tip) of the resected coracoid.

20 Claims, 21 Drawing Sheets

Related U.S. Application Data

(60) Provisional application No. 62/131,099, filed on Mar. 10, 2015.

(51) Int. Cl.

| | | |
|---|---|---|
| *A61B 17/88* | (2006.01) | |
| *A61B 17/16* | (2006.01) | |
| *A61B 17/28* | (2006.01) | |
| *A61B 17/15* | (2006.01) | |
| *A61B 17/56* | (2006.01) | |
| *A61F 2/30* | (2006.01) | |
| *A61F 2/28* | (2006.01) | |
| *A61B 5/107* | (2006.01) | |
| *A61B 90/00* | (2016.01) | |

(52) U.S. Cl.
CPC ........ *A61B 17/282* (2013.01); *A61B 17/2816* (2013.01); *A61B 17/8866* (2013.01); *A61F 2/4644* (2013.01); *A61B 17/151* (2013.01); *A61B 17/1635* (2013.01); *A61B 17/1796* (2013.01); *A61B 2017/564* (2013.01); *A61B 2017/568* (2013.01); *A61B 2090/061* (2016.02); *A61F 2/4612* (2013.01); *A61F 2002/285* (2013.01); *A61F 2002/2835* (2013.01); *A61F 2002/30736* (2013.01); *Y10T 408/567* (2015.01); *Y10T 408/56245* (2015.01)

(58) Field of Classification Search
CPC ... A61B 17/1739; A61B 17/17; A61B 17/151; A61B 17/8095; A61B 17/1778; A61B 17/56; A61B 17/1635; A61B 2017/564; A61B 2017/568; A61B 2017/2926; A61B 2017/2808; A61B 2090/061; A61F 2/4644; A61F 2/4612; A61F 2002/30736; A61F 2002/285; A61F 2002/2835; Y10T 408/56245; Y10T 408/567
USPC ................................. 606/80, 96, 87, 98, 53
See application file for complete search history.

(56) References Cited

U.S. PATENT DOCUMENTS

| | | | | |
|---|---|---|---|---|
| 2009/0318977 | A1* | 12/2009 | Di Giacomo | A61B 17/809 606/86 R |
| 2010/0069974 | A1* | 3/2010 | Oren | A61B 17/1684 606/86 R |
| 2011/0270255 | A1* | 11/2011 | Smith | A61B 17/1684 606/80 |
| 2013/0066371 | A1* | 3/2013 | Rogers | A61F 2/4081 606/232 |
| 2013/0238099 | A1* | 9/2013 | Hardy | A61F 2/4081 623/19.11 |
| 2016/0374694 | A1* | 12/2016 | Haberman | A61B 17/1635 606/80 |
| 2017/0112625 | A1* | 4/2017 | Taverna | A61F 2/4644 |

* cited by examiner

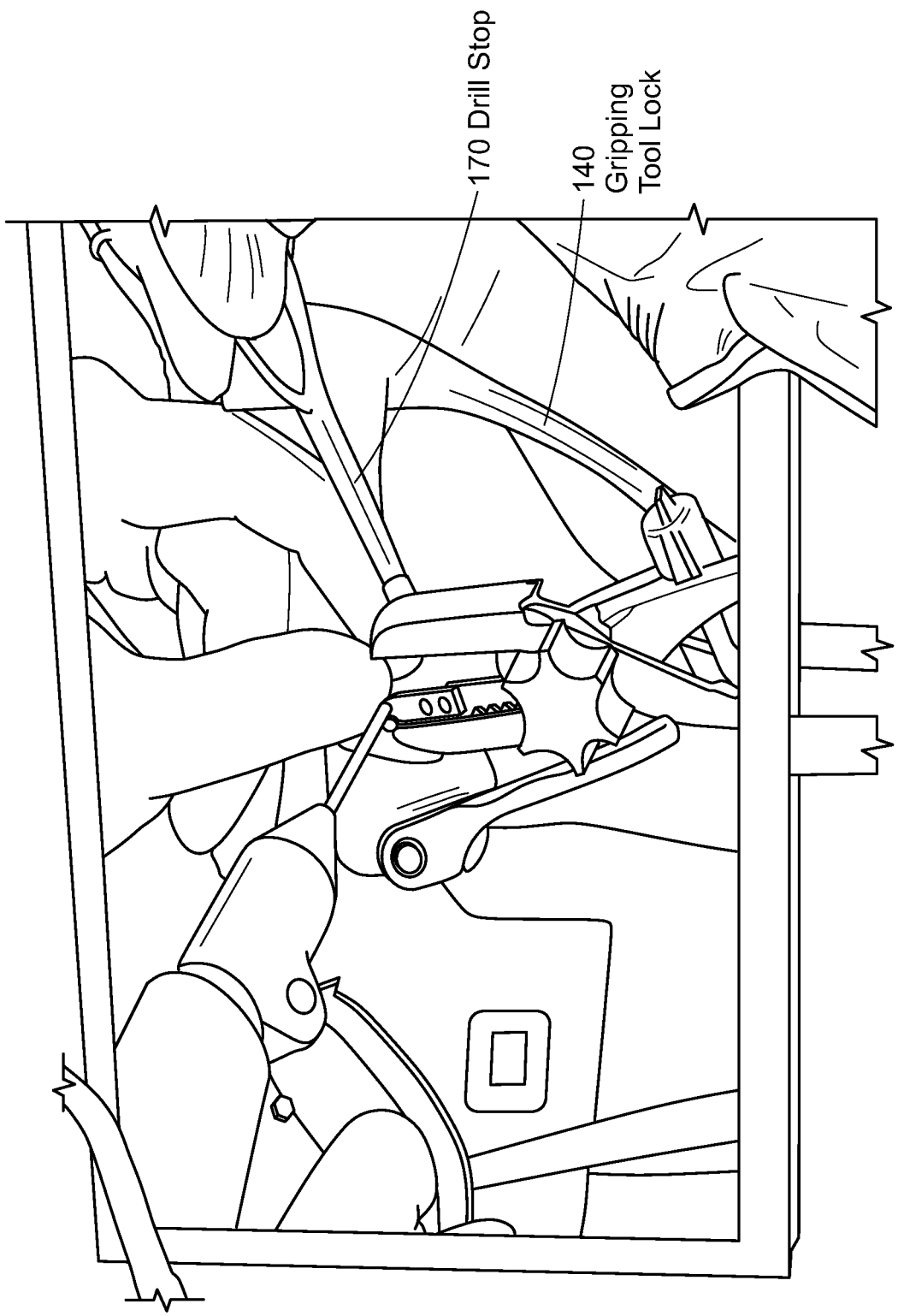

OPEN LATARJET FOR CORRECTION OF ANTERIOR-INFERIOR GLENOID BONE LOSS

CROSS-REFERENCE TO RELATED APPLICATIONS

The subject application is a divisional of co-pending U.S. application Ser. No. 15/555,223, which is a U.S. national stage application under 35 U.S.C. 371 of International Application No. PCT/US16/21705 which was filed on Mar. 10, 2016, which in turn relates and claims priority to U.S. Provisional Application Ser. No. 62/131,099 which was filed Mar. 10, 2015 and is also entitled "OPEN LATARJET FOR CORRECTION OF ANTERIOR-INFERIOR GLENOID BONE LOSS," the contents of which are hereby incorporated herein in their entirety for all purposes.

TECHNICAL FIELD

The subject application relates to surgical systems and methods and more particularly, to improved apparatus, systems and methods for performing an open Latarjet type surgical procedure, e.g., in order to correct for glenoid bone loss. A Latarjet procedure may generally involve the removal and transfer of a section of the coracoid process and its attached muscles to the front of the glenoid so as to prevent further dislocation of the shoulder joint. In particular, the transferred section of the coracoid advantageously acts as a bone block which physically prevents the shoulder from clipping out of the socket. Moreover, the muscle transfer may advantageously provide additional stability to the joint.

BACKGROUND

The shoulder joint, also referred to as the glenohumeral joint, is the joint between the glenoid cavity (a part of the scapula) and the head of the humerus (upper arm bone). The glenoid cavity is shallow, covering only about a third of the head humeral head. As a result, the glenoid cavity provides relatively little bony constraint upon motion of the humerus and the glenohumeral joint exhibits the widest range of motion of all joints in the human body.

While the glenohumeral joint is also constrained by soft tissue (e.g., cartilage attached to the rim of the glenoid cavity, tendons, etc.), in general, soft tissue cannot provide the same degree of constraint as bone. Accordingly, it is relatively easy to force the humerus from its normal anatomical position with respect to the glenoid socket (i.e., dislocate the shoulder). While not life threatening, a dislocated shoulder can cause pain and immobilization of the joint, impacting a patient's lifestyle.

In the case of severe bone loss, a surgeon may perform a "Latarjet procedure" to repair glenohumeral instability. As noted above, in a Latarjet procedure, a surgeon may attempt to restore bone mass to the glenoid cavity by securing a bone graft to the surface of the glenoid suffering bone loss. When successful, the bone graft acts as a scaffold, allowing the glenoid bone to grow into the bone graft and restore the lost glenoid bone mass (bone fusion). The bone graft may typically be taken from a portion of the patient's scapula referred to as the coracoid process or simply coracoid, with muscles still attached to the coracoid. Thus, when the coracoid graft is fused to the glenoid cavity, the muscles attached to the coracoid may provide further constraint upon the glenohumeral joint.

SUMMARY

In an embodiment, a coracoid resection guide is provided. The coracoid resection guide includes a gripping tool and an alignment guide. The gripping tool includes a pivotably actuatable jaw at a distal end, the jaw including a first jaw portion and a second jaw portion. The first jaw portion includes a first gripping surface and a first planar surface approximately perpendicular thereto. The second jaw portion includes a second gripping surface and a second planar surface approximately perpendicular thereto. The gripping tool further includes a pivot mounting the first jaw portion to the second jaw portion such that the first and second gripping surfaces face one another and define a gripping area there-between, the gripping area dimensioned for receipt of a coracoid process, the first planar surface and the second planar surface lying in the same plane and a tool axis extends through the pivot and the gripping area. The alignment guide includes an elongated guide body extending between a first end and a second end along a guide axis and at least two guide holes extending through the thickness of the guide body, where each of the guide holes positioned along the guide axis and distanced apart. The alignment guide is mounted to the gripping tool pivot adjacent the first end such that the at least two guide holes extend approximately perpendicular to the plane of the first and second planar surfaces of the jaw, the alignment guide is rotatable about the pivot between the tool axis and a selected angle; and the alignment guide is capable of linear translation along the guide axis.

Embodiments of the coracoid resection guide may include one or more of the following, in any combination.

In an embodiment, the coracoid resection guide further includes a locking mechanism for securing the alignment guide at a selected location with respect to the gripping tool.

In an embodiment of the coracoid resection guide, the at least two guide holes extend through a boss extending from surface of the alignment guide opposite the jaw.

In an embodiment, a method of joint repair is provided. The method includes providing a bone graft, forming an approximately planar surface on the bone graft, and forming a proximal hole and a distal hole through the bone graft. The proximal and distal holes are oriented approximately perpendicular to the planar surface of the bone graft. The proximal hole is positioned closer to a cut end of the bone graft than the distal hole. The method further includes forming a first hole in patient's glenoid, securing the bone graft to the patient's glenoid at the first glenoid hole by a first fastener extending through the distal bone graft hole and the first glenoid hole, rotating the bone graft about the first fastener to orient the proximal bone graft hole to overlie the patient's glenoid, inserting a bone removal tool through the proximal bone graft hole after said rotation, and securing the bone graft to the patient's glenoid at the proximal bone graft hole by a second fastener extending through the proximal bone graft hole.

Embodiments of the method may include one or more of the following, in any combination.

In an embodiment of the method, the first glenoid hole is not formed concurrently with either the proximal or distal bone graft hole.

In an embodiment of the method, the bone graft is a resected coracoid.

In an embodiment, the method further includes forming a second hole in the patient's glenoid by the bone removal tool, wherein the second glenoid hole is superior to the first glenoid hole and wherein the superior glenoid hole is formed after the inferior glenoid hole.

In an embodiment of the method, the inferior and superior glenoid holes are formed at a selected angle and lateral offset with respect to an articular surface of the glenoid.

In an embodiment of the method, the selected angle is chosen within the range between about 5 degrees to about 45 degrees.

In an embodiment of the method, the selected angle is about 10 degrees.

In an embodiment of the method, the selected lateral offset is chosen within the range between about 5 mm to about 8 mm.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIG. 7 illustrates use of the coracoid resection guide of the embodiment of FIG. 6 for drilling holes through a coracoid process;

DETAILED DESCRIPTION

Figure 1:
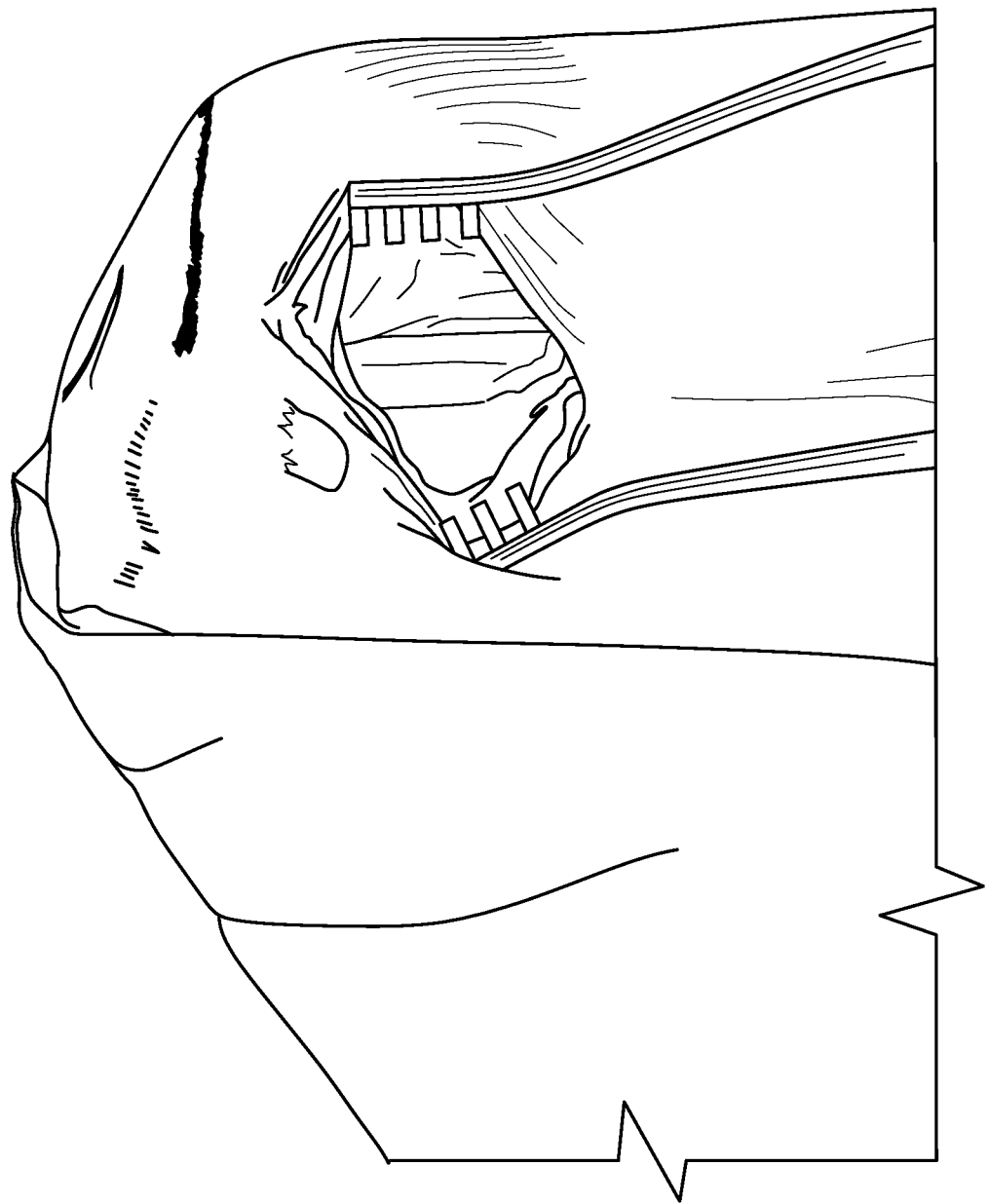
FIG. 1 illustrates formation of a portal for accessing a corocoacromial (CA) ligament in an embodiment of an open Latarjet procedure.

As noted above, the subject application relates to improved apparatus, systems and methods for performing an open Latarjet type surgical procedure, e.g., in order to correct for glenoid bone loss. In example embodiments of a Latarjet type surgical procedure the coracoid may typically secured to the glenoid by screws. In particular, a surgeon may drill two or more holes into each of the coracoid and the glenoid and align the coracoid and glenoid holes. Subsequently, screws may be positioned within the bone holes for fixation. Notably, in such procedures, a likelihood of successful bone fusion may depend upon orientation and alignment of the coracoid and glenoid holes for positioning of the coracoid graft surface on the glenoid graft surface. For example, if the coracoid and glenoid bone holes are misaligned, it may result in poor contact between the glenoid and coracoid graft surfaces or insufficient contact pressure at the graft interface thereby reducing a likelihood of successful bone fusion. Thus, improved apparatus, systems and methods are presented herein for facilitating coracoid resection, e.g., so as to ensure a flush interface surface. Moreover improved apparatus, systems and methods are presented herein for facilitating proper drilling and alignment of holes in the coracoid and the glenoid for fixation of the coracoid to the glenoid.

Embodiments of the present disclosure are directed to instrumentation that facilitate coracoid-glenoid fixation in Latarjet procedures. For example, a single instrument, a coracoid resection tool, may be provided/utilized to prepare a coracoid bone graft for size, flatness, and hole drilling. A glenoid drill guide may further be provided/utilized that uses sized offsets for placement of the coracoid graft flush with the glenoid.

Further embodiments of the disclosure are directed to corresponding methods that employ this instrumentation. For example, a surgeon may employs the coracoid resection tool as a guide to plane the inferior coracoid surface that will serve as the coracoid graft surface. The coracoid resection tool may further guide the placement of coracoid holes along the length of the coracoid and orient the holes approximately perpendicular to the planed coracoid graft surface. For example a proximal coracoid hole may be positioned towards the proximal end (i.e., the cut end) of the resected coracoid while a distal coracoid hole may be positioned towards the distal end (i.e., the tip) of the resected coracoid.

In exemplary embodiments, after preparation of the coracoid graft, an inferior hole may be formed in the glenoid using an offset glenoid drill guide to space the inferior hole from the glenoid cavity surface. The proximal end of the coracoid may then be provisionally secured to the glenoid graft surface at the inferior glenoid hole using a first fixation member (e.g., a bone screw) while the surgeon rotates the coracoid with respect to the glenoid so that edge of the coracoid is approximately flush with the articular glenoid surface. Subsequently, the distal coracoid hole may be positioned for use as a guide for drilling the superior glenoid hole. After drilling the superior glenoid hole, the distal end of the coracoid may be secured to the glenoid at the superior glenoid hole using a second fixation member (e.g., a second bone screw). Once the coracoid is mounted to the glenoid at both the inferior and superior glenoid holes, the first and second screws may be tightened to apply an appropriate level of pressure for bone fusion.

The methods described herein provide a number of benefits increasing the likelihood of successful bone fusion and simplifying the Latarjet process. In one aspect, the resected coracoid is prepared using a single instrument, reducing surgical time and costs. In another aspect, the coracoid resection guide ensures that the drilled coracoid holes are approximately perpendicular to the planed coracoid graft surface. In an additional aspect, the glenoid drill guide ensures that the holes formed in the glenoid do not impinge the glenoid cavity surface or articular cartilage thereon. In a further aspect, the disclosed methods allows the surgeon to drill the superior glenoid hole using an existing hole formed in the coracoid graft, ensuring that the coracoid and glenoid holes are axially aligned.

Figure 2:
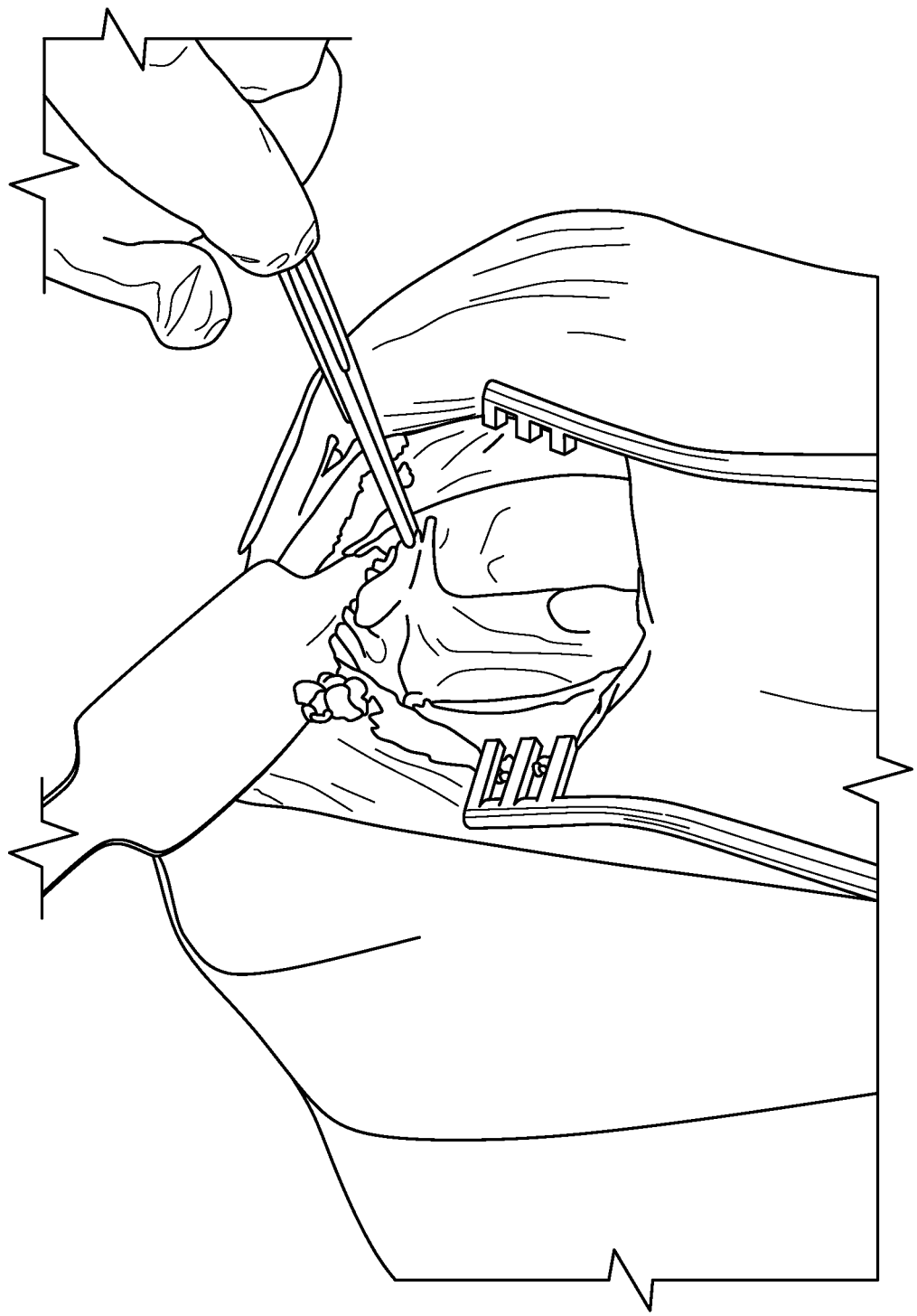
FIG. 2 illustrates exposing the CA ligament in an embodiment of an open Latarjet procedure.
Figure 3:
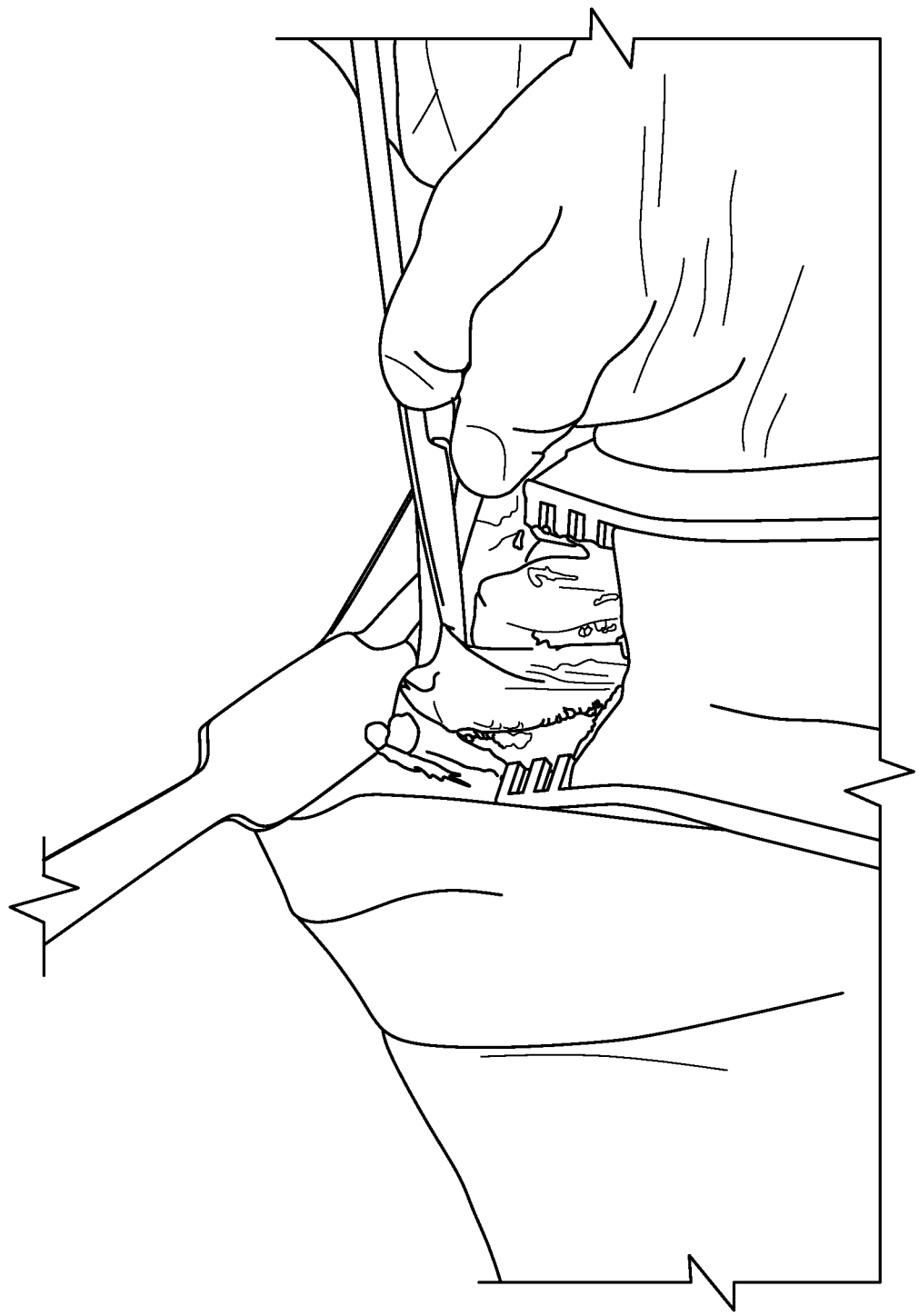
FIG. 3 illustrates cutting the CA ligament adjacent the coracoid process in an embodiment of an open Latarjet procedure.
Figure 4:
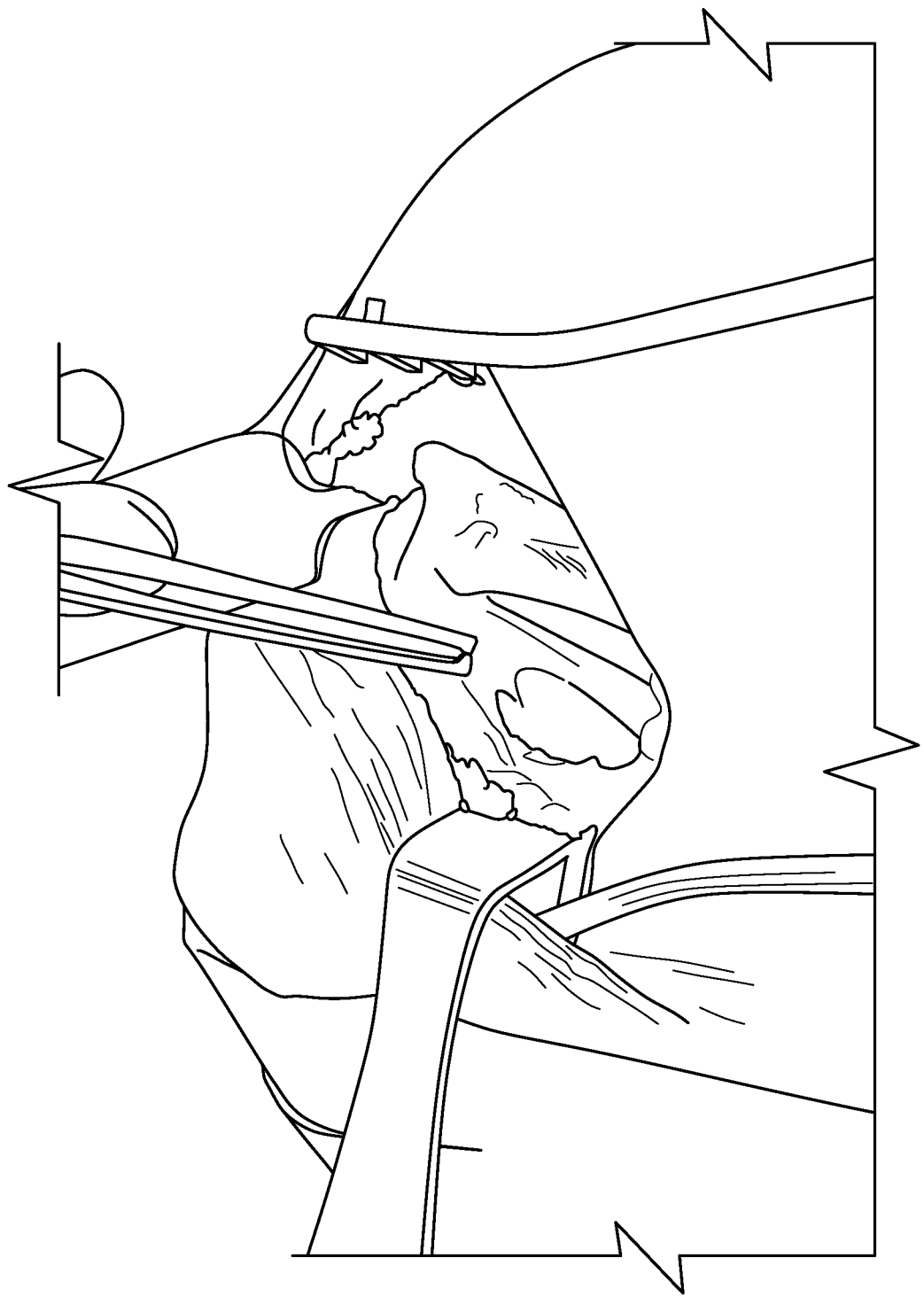
FIG. 4 illustrates removing the pectoralis minor muscle from the coracoid process in an embodiment of an open Latarjet procedure.
Figure 5:
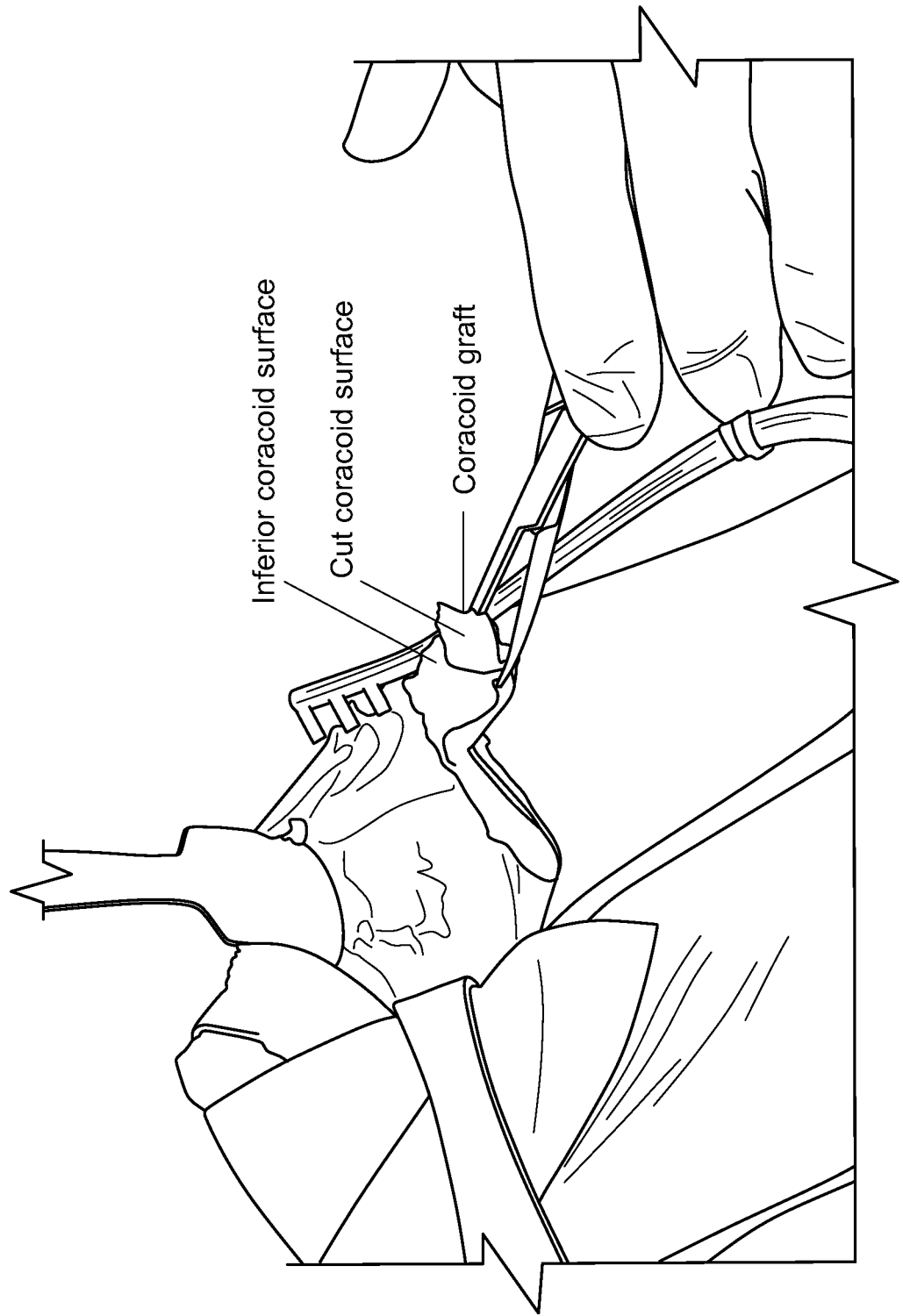
FIG. 5 illustrates resection of a coracoid process in an embodiment of an open Latarjet procedure.

The discussion will now turn to the figures, beginning with FIGS. 1-5, which illustrate preparation of the glenohumeral joint for Latarjet repair according to embodiments of the disclosure. FIG. 1 illustrates a portal formed in patient's shoulder for access to the corocoacromial (CA) ligament, e.g., utilizing an anterior deltopectoral approach. The portal may be formed, e.g., by cutting an incision in the patient's shoulder, e.g., extending on a diagonal defined between the coracoid process and the proximal humeral shaft. In alternative embodiments, other types of incisions, e.g., a vertically aligned incision such as extending from the coracoid towards the axillary fold, curved incision or other type of incision may be used instead. An incision retractor may then be used to open the incision and allow for access to the CA ligament. FIG. 2 illustrates exposure of the CA ligament. In some embodiments, the patient's arm may be placed in external rotation with abduction applied to better expose the CA ligament. FIG. 3 illustrates transection of the CA ligament near the coracoid. FIG. 4 illustrates removal of the pectoralis minor muscle from the coracoid. Note that care may be taken to not release the muscle past the tip of the coracoid and damage remaining blood supply to the coracoid. FIG. 5 illustrates a result of a coracoid resection with the coracoid still attached to the corocoacromial ligament. As illustrated, the resultant coracoid graft includes a cut coracoid surface, transverse to the inferior coracoid surface.

Figure 6:
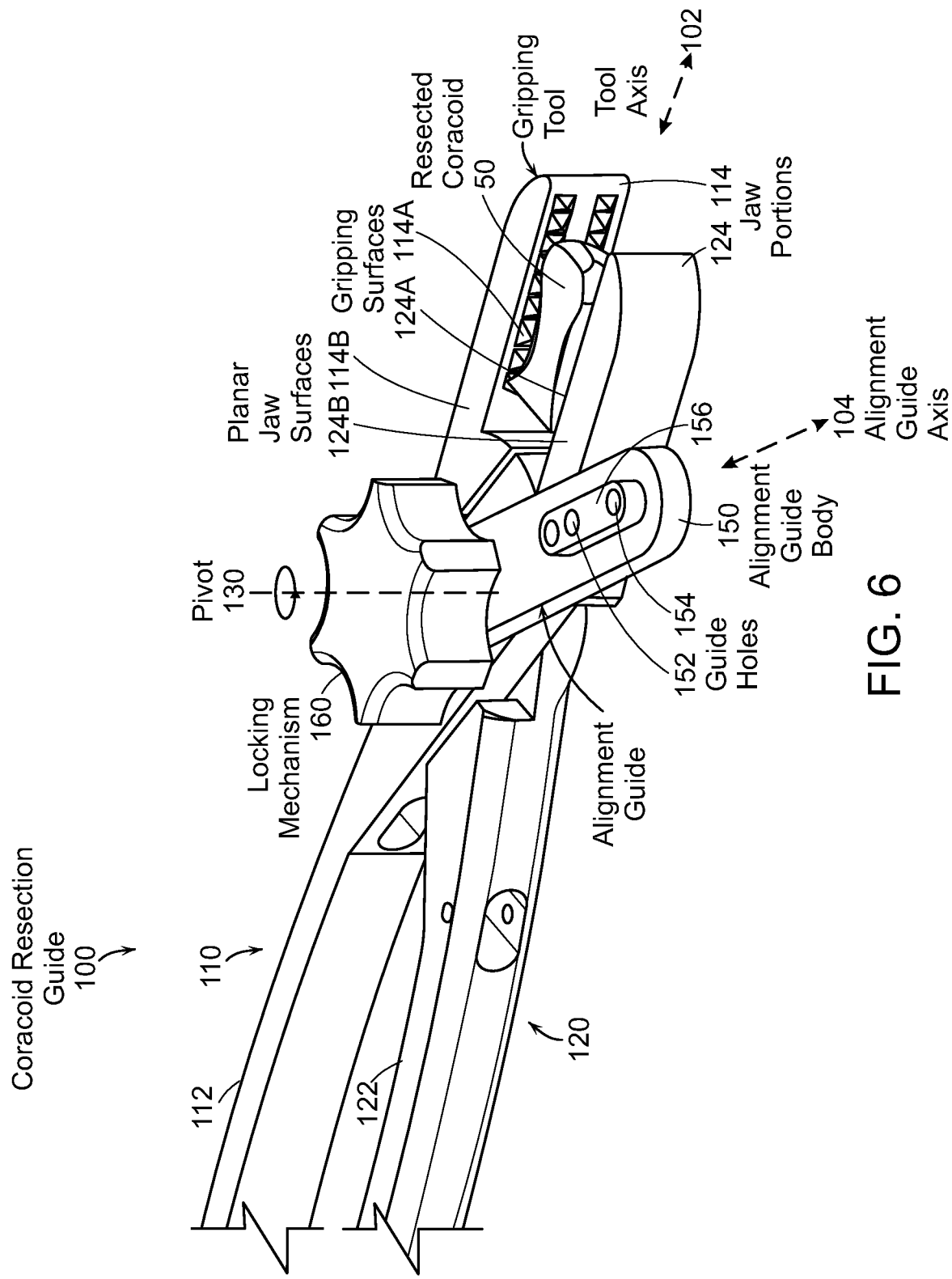
FIG. 6 is a schematic illustration of an embodiment of a coracoid resection guide for use in an embodiment of an open Latarjet procedure.

FIG. 6 illustrates an embodiment of a coracoid resection guide 100 for use in preparation of the resected coracoid. The resection guide 100 advantageously includes both a gripping tool and an alignment guide, advantageously allowing for a dual functionality of the guide as described herein. In particular, as described herein, the gripping tool may secure the resected coracoid to the tool and facilitates planarization of the coracoid graft surface while the alignment guide may provides an adjustable template for forming holes through the coracoid, e.g., approximately perpendicular to the coracoid graft surface once planed.

As illustrated, the gripping tool is generally elongated and formed from two members 110 and 120. A first elongated member 110 includes a first handle portion 112 at its proximal end and a first jaw portion 114 at its distal end. A second elongated member 120 includes a second handle portion 122 at its proximal end and a second jaw 124 portion at its distal end. The first and second handle portions 112 and 122 form a handle of the gripping tool and the first and second jaw 114 and 124 portions form a jaw of the gripping tool. The first jaw portion 114 includes a first gripping surface 114A and a first planar surface 114B approximately perpendicular thereto. The second jaw portion 124 includes a second gripping surface 124A and a second planar surface 124B approximately perpendicular thereto. The first and second elongated members 110 and 120 are mounted to one another at a pivot 130 positioned proximal to the first and second jaw portions. So mounted, the first and second gripping surfaces 114A and 124A face one another and define a gripping area there-between, where the gripping area is dimensioned for receipt of a coracoid 50. The first and second planar surfaces 114B and 124B are further oriented in a same plane. A tool axis 102 further extends longitudinally, through the pivot and gripping area.

The alignment guide includes an elongated guide body 150 extending between a first end and a second end along a guide axis 104. At least two guide holes 152 and 154 are formed through the thickness of the guide body for use in forming the proximal and distal holes in the coracoid graft. Each of the guide holes 152 and 154 are positioned along the length of the guide axis 104 and distanced apart from one another. In certain embodiments, the proximal and distal coracoid guide holes 152 and 154, respectively, are spaced approximately 10 mm apart. Optionally, the alignment guide may further include a raised boss 156 projecting outward from a face of the alignment guide body 150 opposite a side of the body facing the gripping tool. The proximal and distal guide holes 152 and 154, respectively, may be formed through the boss 156 in order to facilitate straight drilling (e.g., by increasing length of the guide holes through the alignment guide. In further embodiments, three or more guide holes may be formed, providing the ability to drill guide holes spaced by larger separations in order to accommodate unusually long coracoid grafts.

Advantageously the guide body 150 may be pivotably mounted to the gripping tool in common alignment with at the gripping tool pivot 130, e.g., pivotably mounted adjacent a first (proximal) end of the alignment guide body 150. In exemplary embodiments, when so mounted the longitudinal axes of at least two guide holes 152 and 154 are advantageously oriented approximately perpendicular to the plane of the first and second planar surfaces 114A and 114B of the jaw. In some embodiments, the guide body 150 may be capable of linear translation along the guide axis 104, e.g., relative to the gripping tool.

Advantageously, a locking mechanism 160 may further provided to secure the alignment guide in place with respect to the gripping tool. For example, a locking knob 160 is illustrated in FIG. 6. However, in alternative embodiments, other locking mechanisms may be employed without limit. The locking mechanism may advantageously be used to set the angle between the longitudinal axis 102 of the gripping tool and the guide axis 104 of the alignment guide. Moreover, the locking mechanism set a translational position of the guide body 150 along the guide axis 104 relative to the locking tool.

FIG. 7 (which is referenced herein in conjunction with reference to FIG. 6) illustrates an embodiment of the coracoid guide 100 in use. The coracoid 50 is positioned between the first and second gripping surfaces 114A and 124A of the jaw and the first and second handle portions 112 and 122 are squeezed towards one another to urge the first and second gripping surfaces 114A and 124A together, securing the coracoid 50 by compression within the gripping area. Optionally, the gripping tool may further include a gripping tool lock mechanism 140 for maintaining the handle and jaw portions in place. The coracoid 50 is oriented such that the coracoid centerline is generally aligned with the tool axis 102. The inferior surface of the coracoid graft (also referred to as the coracoid graft surface) is further positioned such that it is raised above the plane of the first and second planar surfaces of the jaw 114B and 124B. While not shown in FIG. 7, after the coracoid graft is secured to the coracoid drill guide, the coracoid graft surface may be planed by a rasp or other bone removal tool such that it is approximately flush and planar with the plane of the first and second planar surfaces of the jaw 114B and 124B. That is to say, the first and second planar surfaces of the jaw are used as a reference to plane the coracoid graft surface.

FIG. 7 further illustrates a surgeon drilling a hole through the coracoid. Note that the alignment guide body 150 has been rotated about the pivot 130, such that the guide axis 104 is oriented approximately parallel to the coracoid centerline, e.g., parallel to the longitudinal axis of the gripper tool. Moreover, the alignment guide body 150 has been translated along the guide axis 104 such that each of the guide holes 152 and 154 overlie the coracoid graft surface. Subsequently, the alignment guide is locked in place using the locking mechanism 160. As discussed herein, the guide holes 152 and 154 extend through the guide body 150 approximately perpendicular to the plane of the first and second planar surfaces 114B and 134B of the jaw. Accordingly, a hole that is drilled through the coracoid using the guide holes 152 and 154 will also be oriented approximately perpendicular to the plane of the inferior coracoid graft surface. A drill stop 170 may be further provided to prevent damage to surrounding tissue and bone when drilling the coracoid.

The discussion will now turn to FIGS. 8-13, which illustrate exemplary instruments and methods for preparing the glenoid to receive the coracoid graft. In FIG. 8A, a plurality of retractors 202 are illustrated for moving the humeral head 210 and tissue surrounding the humerous and glenoid cavity 212, allowing access to the glenoid graft surface 214. FIG. 8B, illustrates an offset measurement tool 220 for use in measuring the coracoid. The offset measurement tool 220 includes an elongated shaft 222 and a gauge 224 at the distal end. The gauge 224 includes a distally extending prong 224A and a plurality of laterally extending fingers 224B each of a different known length. In use, the prong 224A is inserted into the distal coracoid hole and the shaft 222 is rotated to compare the relative length of the fingers 224B to the lateral edge of the resected coracoid. In this manner, the length of the finger that terminates closest to the lateral edge of the resected coracoid is taken to be the offset distance between the distal coracoid hole and the coracoid lateral edge. This offset distance is subsequently used for selecting a glenoid guide, as described herein.

Figure 9:
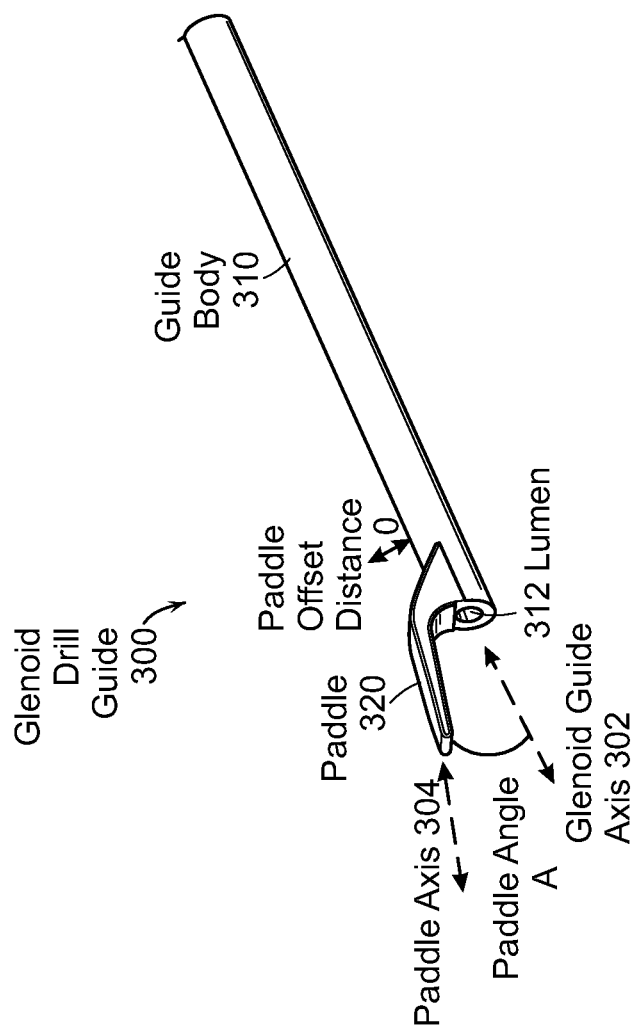
FIG. 9 is a schematic illustration of an embodiment of a glenoid drill guide for use in an embodiment of an open Latarjet procedure.

FIG. 9 illustrates an embodiment of a glenoid guide 300 for use in forming a bone hole in the glenoid. The glenoid guide 300 includes a generally elongated, tubular guide body 310 having an internal lumen 312 extending along a longitudinal glenoid guide axis 302 between a proximal end and a distal end. The glenoid guide 300 further includes a paddle 320 mounted at the distal end of the guide 300 at an offset and extending along a paddle axis 304. An offset angle A between the paddle axis 304 and the guide axis 302 is selected within the range between about 5° to about 20°. In certain embodiments the paddle offset angle 306 is about 10°. The offset distance D by which the paddle 320 is offset from the guide axis 302 is selected within the range between about 5 mm to about 8 mm, based upon the offset distance measured by the offset measurement tool 220, as discussed above with respect to FIG. 8B.

Figure 10:
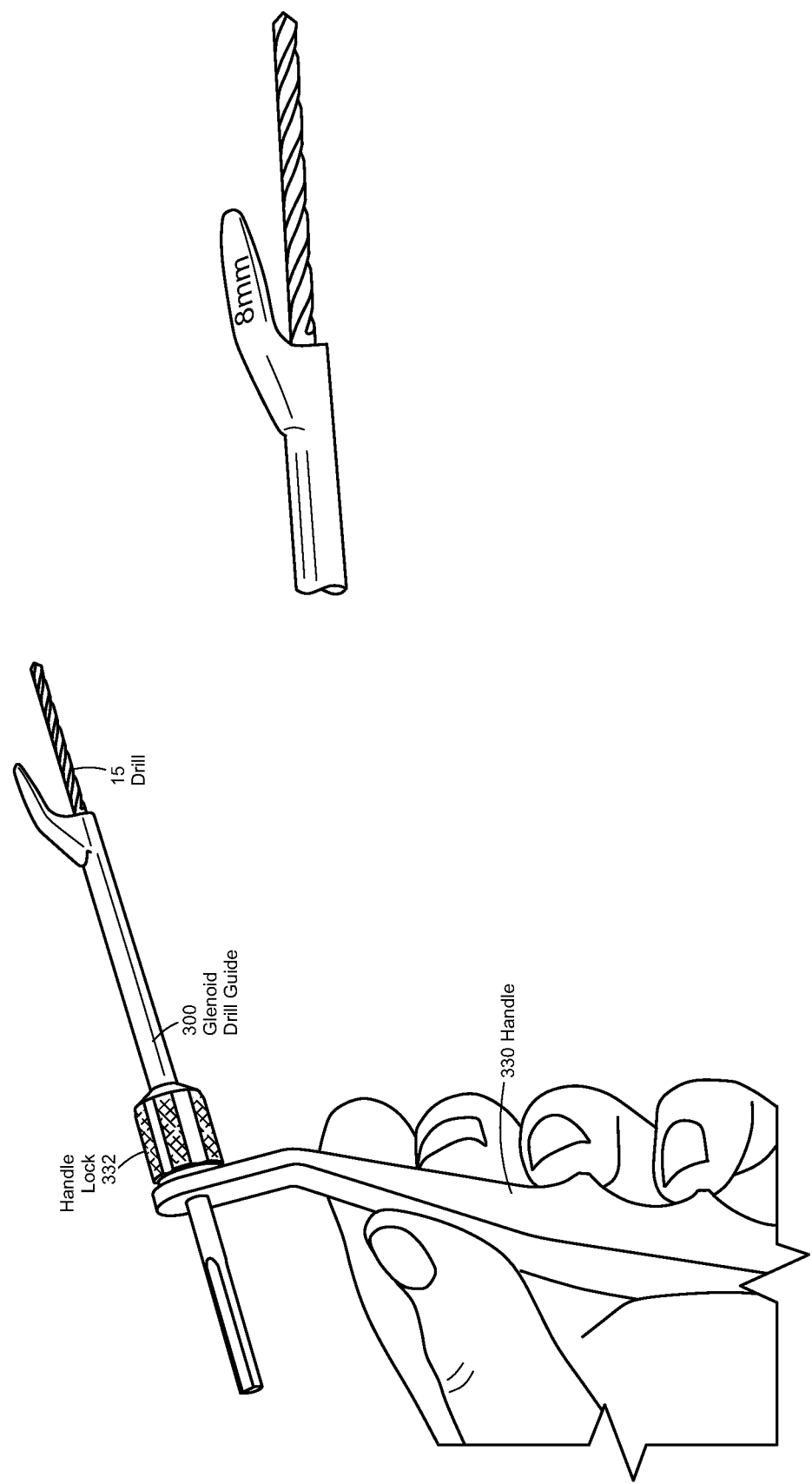
FIG. 10 illustrates the glenoid drill guide of the embodiment of FIG. 9 mounted to a handle.

FIG. 10 illustrates an embodiment of the glenoid guide 300 mounted to a handle 330 and a drill 15 extending through the guide lumen 312. The handle 330 may advantageously rotationally engage the glenoid drill guide, allowing the surgeon to orient the paddle 320 with respect to the glenoid. A handle lock 332 is further illustrated for securing the glenoid drill guide 300 in place with respect to the handle 330.

Figure 11:
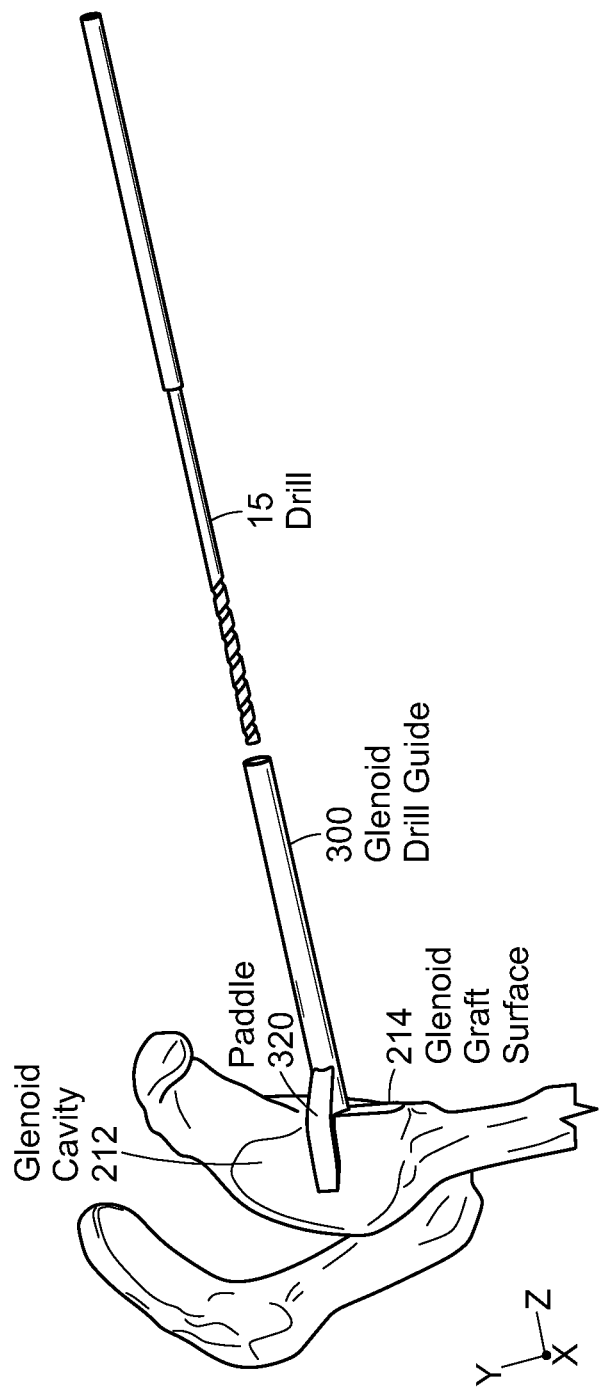
FIG. 11 is a schematic illustration of use of the glenoid drill guide of the embodiment of FIG. 9 used to drill a glenoid hole in an embodiment of an open Latarjet procedure.

FIG. 11 (which is referenced herein in conjunction with reference to FIGS. 8A and 9) is a schematic illustrating the glenoid guide 300 positioned on the glenoid for formation of an inferior hole in the glenoid. The inward facing surface of the paddle 320 is placed against the glenoid cavity 212, with the distal end of the glenoid guide 300 contacting the glenoid graft surface 214. So positioned, the guide lumen 312 is distanced from the glenoid cavity surface by the paddle offset distance and oriented at the offset angle 306 with respect to the glenoid cavity surface for drilling the inferior glenoid hole. Beneficially, this placement allows a surgeon to form the inferior glenoid hole without concern of impinging the glenoid cavity surface and causing further harm to articular cartilage thereon.

Figure 8A:
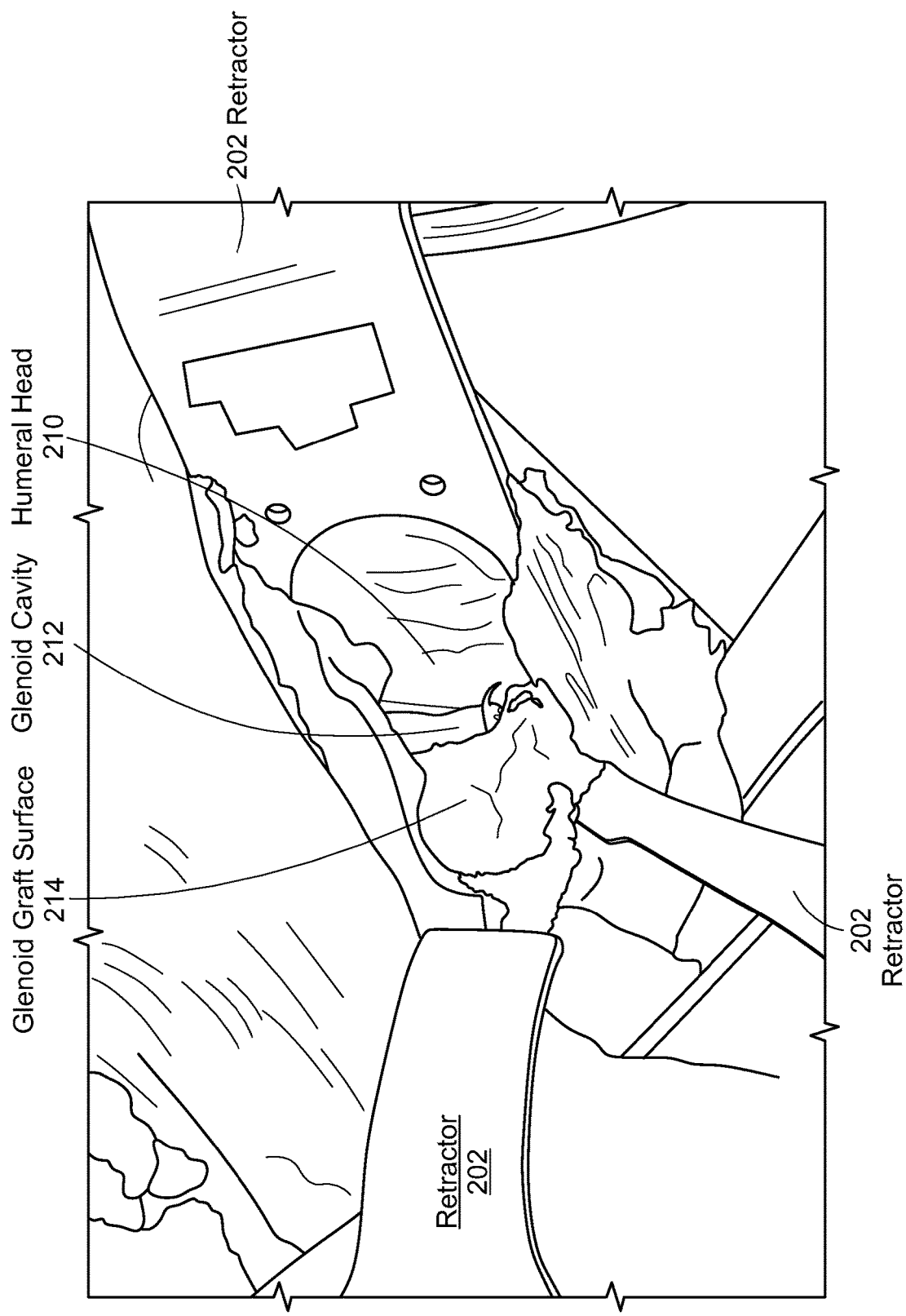
FIG. 8A illustrates preparation of a glenoid in an embodiment of an open Latarjet procedure.
Figure 8B:
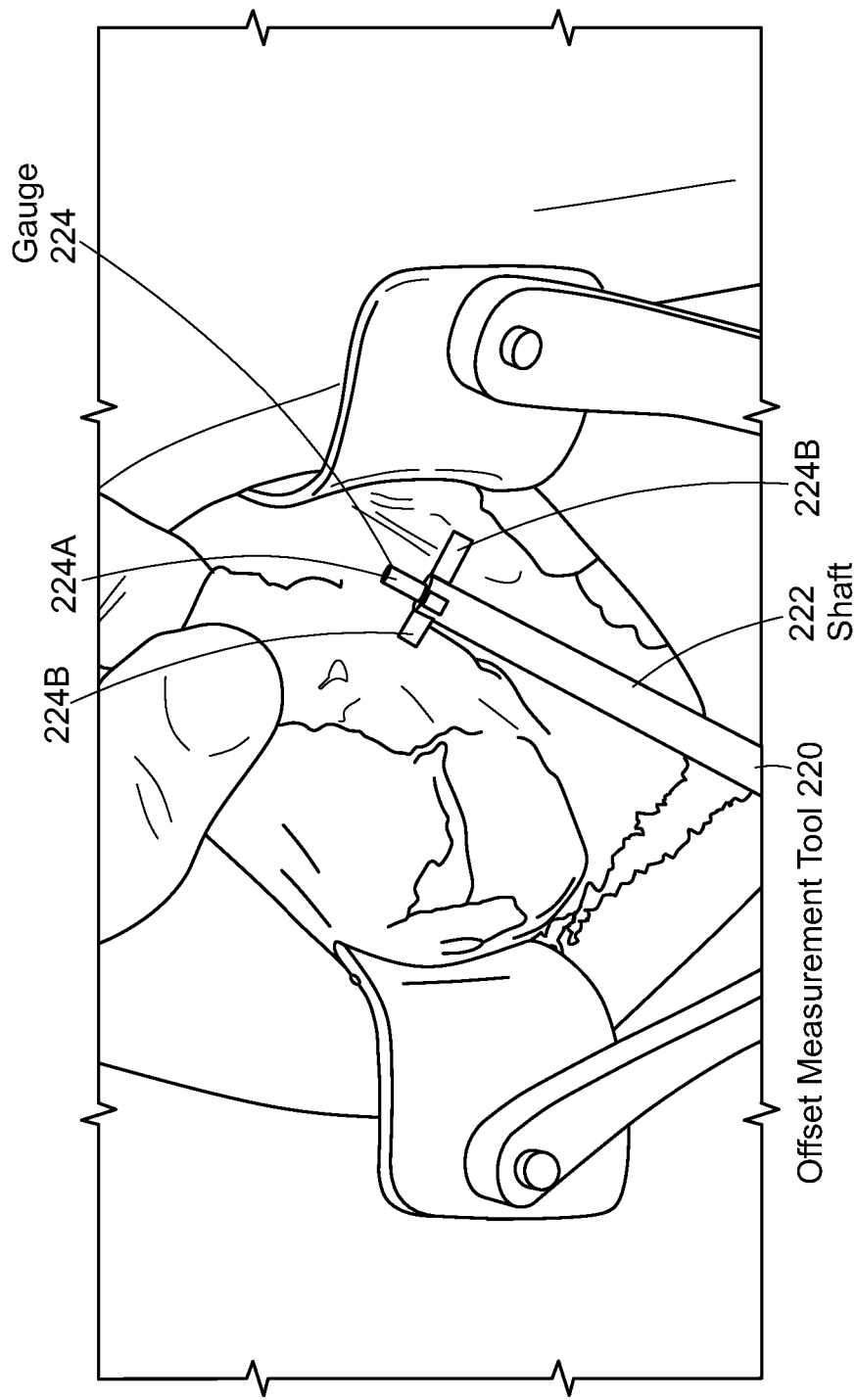
FIG. 8B illustrates an embodiment of an offset measurement tool for measuring an offset distance between a coracoid hole and a coracoid edge.
Figure 12:
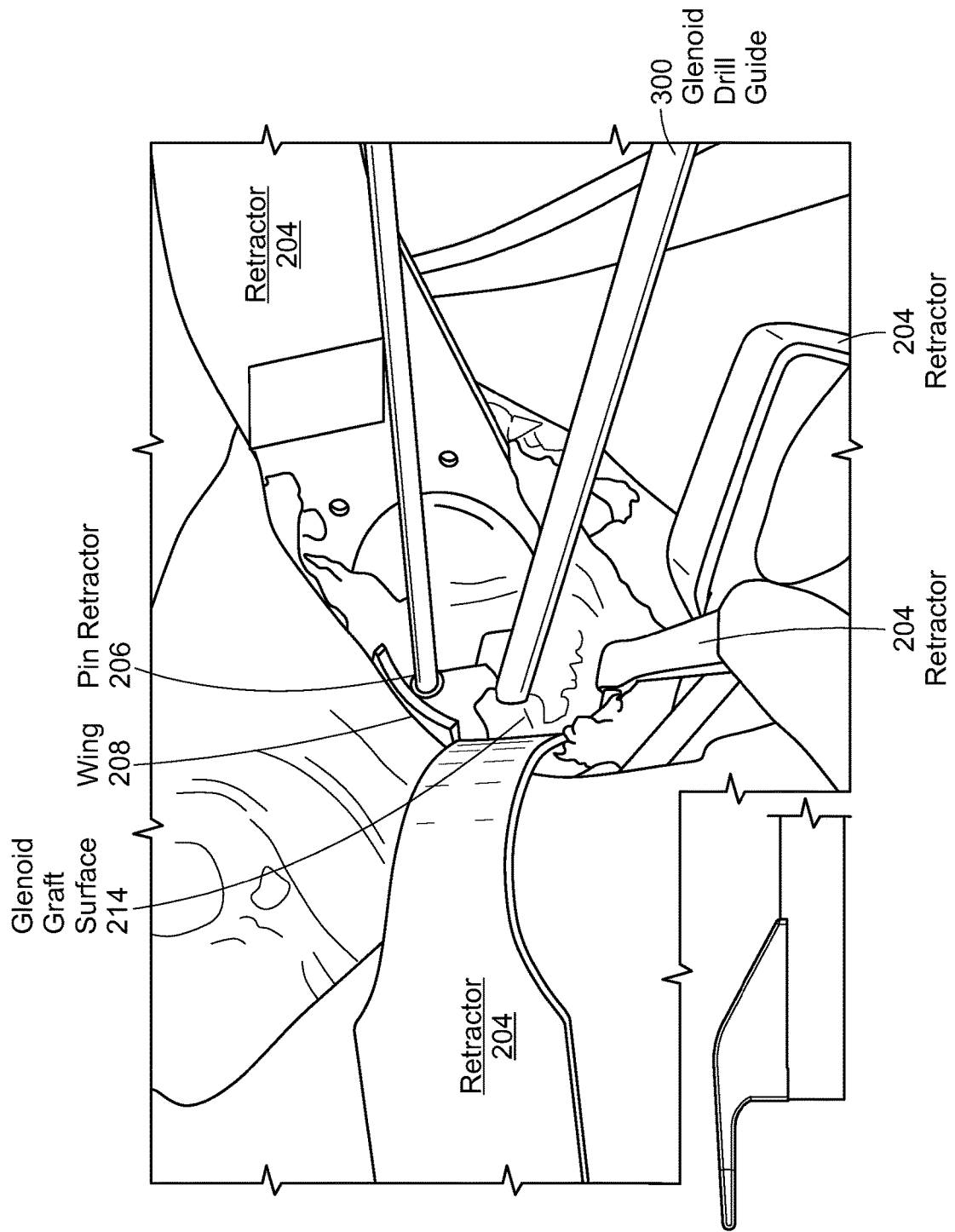
FIG. 12 illustrates use of the glenoid drill guide of the embodiment of FIG. 9 used to drill a glenoid hole in combination with a plurality of tissue retractors in an embodiment of an open Latarjet procedure.
Figure 13:
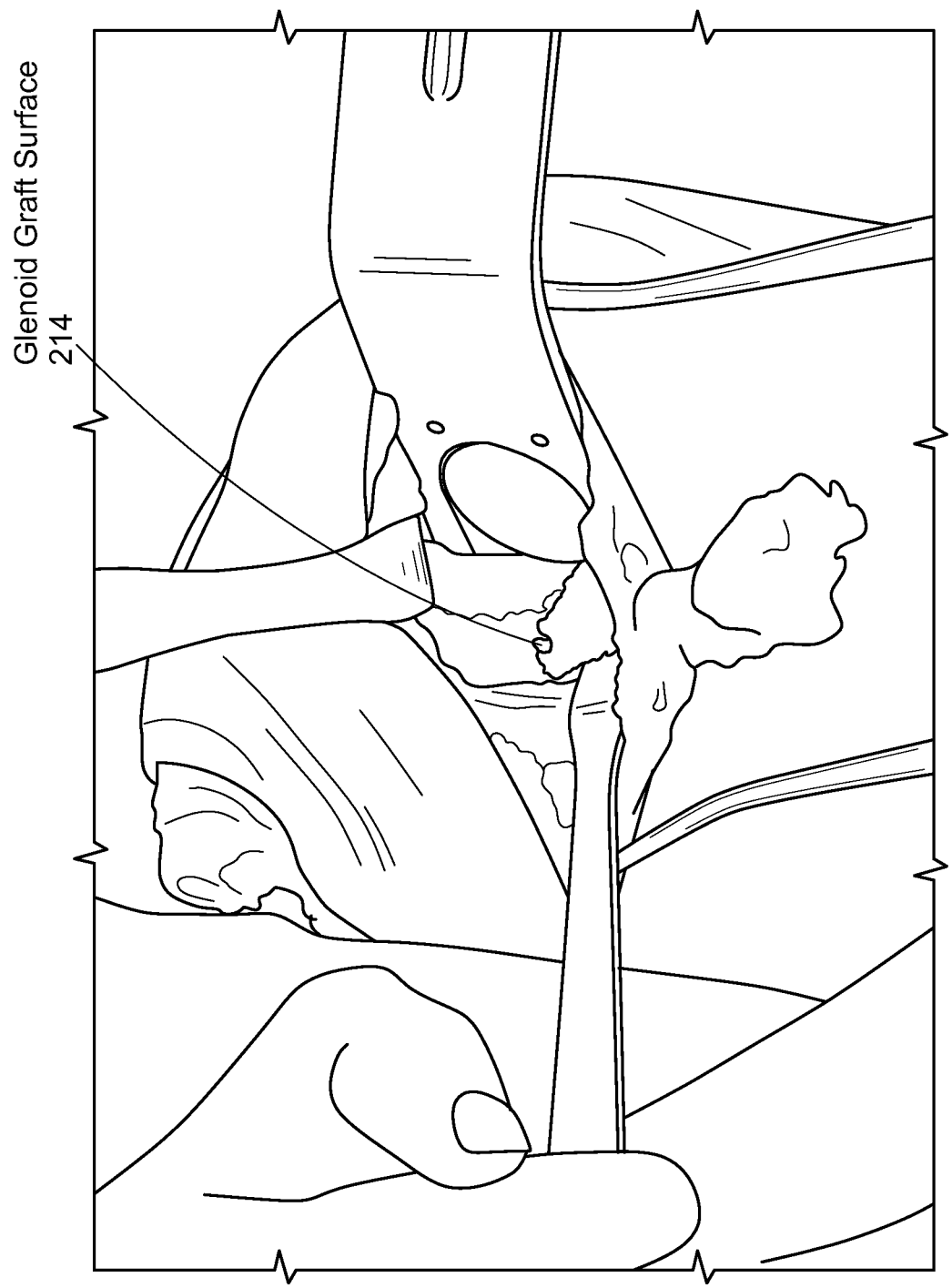
FIG. 13 illustrates the glenoid after drilling an inferior glenoid hole using glenoid drill guide of the embodiment of FIG. 9 in an embodiment of an open Latarjet procedure.

FIGS. 12-13 (which are referenced herein in conjunction with reference to FIGS. 8A, 9 and 11) illustrate use of the glenoid guide 300 in a Latarjet surgery in an embodiment of the disclosure. As in FIG. 11, FIG. 12 illustrates the inward facing surface of the paddle 320 placed against the glenoid cavity 212, with the distal end of the glenoid guide 300 contacting the glenoid graft surface 214. FIG. 13 illustrates the glenoid graft surface 314 after the inferior glenoid hole is drilled.

A plurality of retractors 204 are also illustrated in FIG. 12-13 for providing access to the glenoid. Note in particular, that a pin retractor 206 is illustrated in FIG. 12, used in combination with a corresponding wing 208 for retracting tissue (e.g., skin). Notably, while pin retractors are commonly employed in surgical operations, pin retractors are problematic in that flexible soft tissue can deform around them during surgery, draping about the pin, reducing the ability of the pin retractor to retract the tissue from the surgical site. However, use of a wing 208 that is mechanically coupled to the pin retractor 206 (e.g., secured to a tubular sleeve fitting over the pin) provides a broad surface about which to retract the tissue and inhibits draping about the location of interest. In certain embodiments, the pin retractor 206 is employed in combination with the wing 208. In alternative embodiments, the pin retractor 206 may be employed alone.

Figure 14:
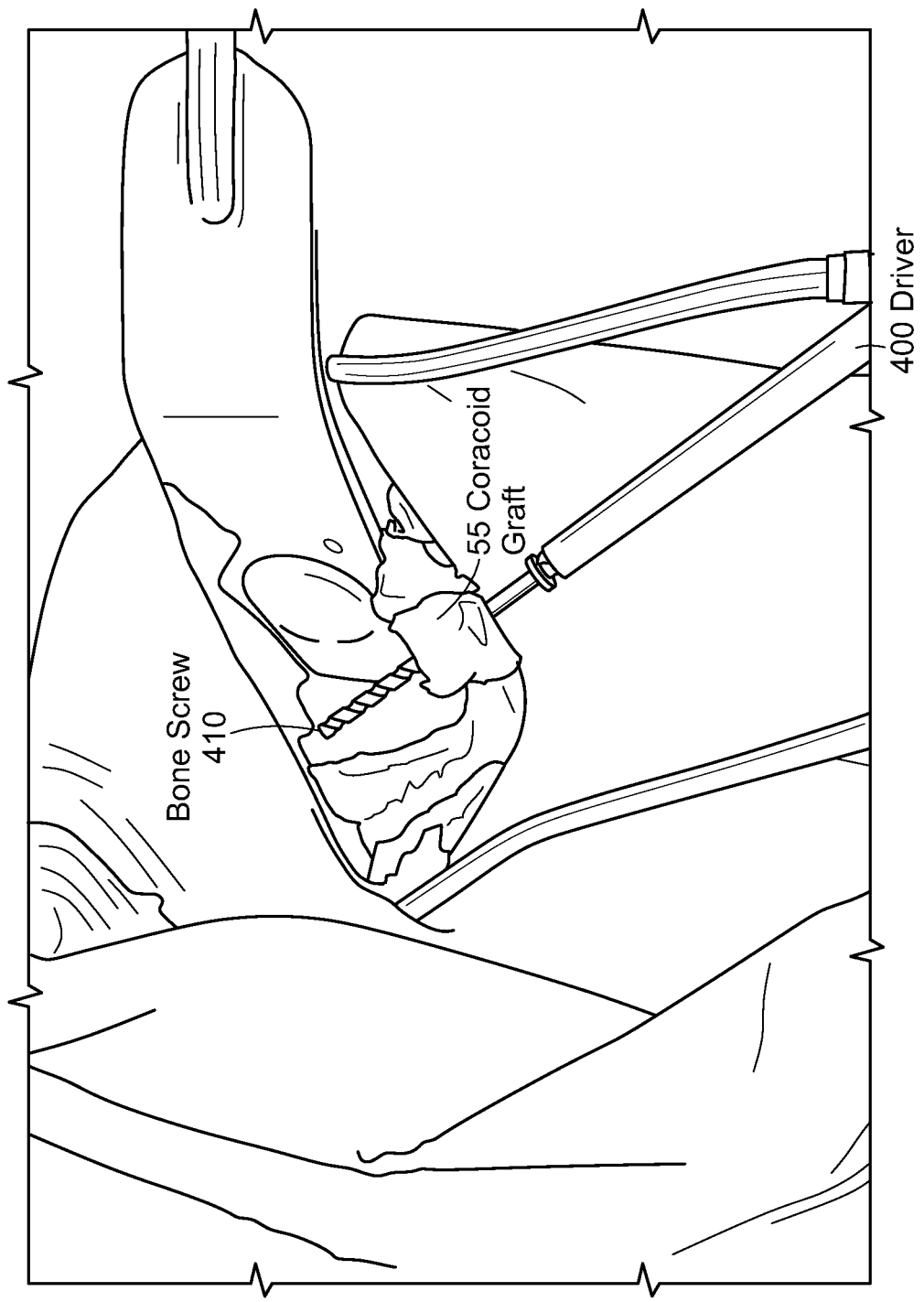
FIG. 14 illustrates the resected coracoid process of FIG. 5 loaded on a screw in an embodiment of an open Latarjet procedure.
Figure 15:
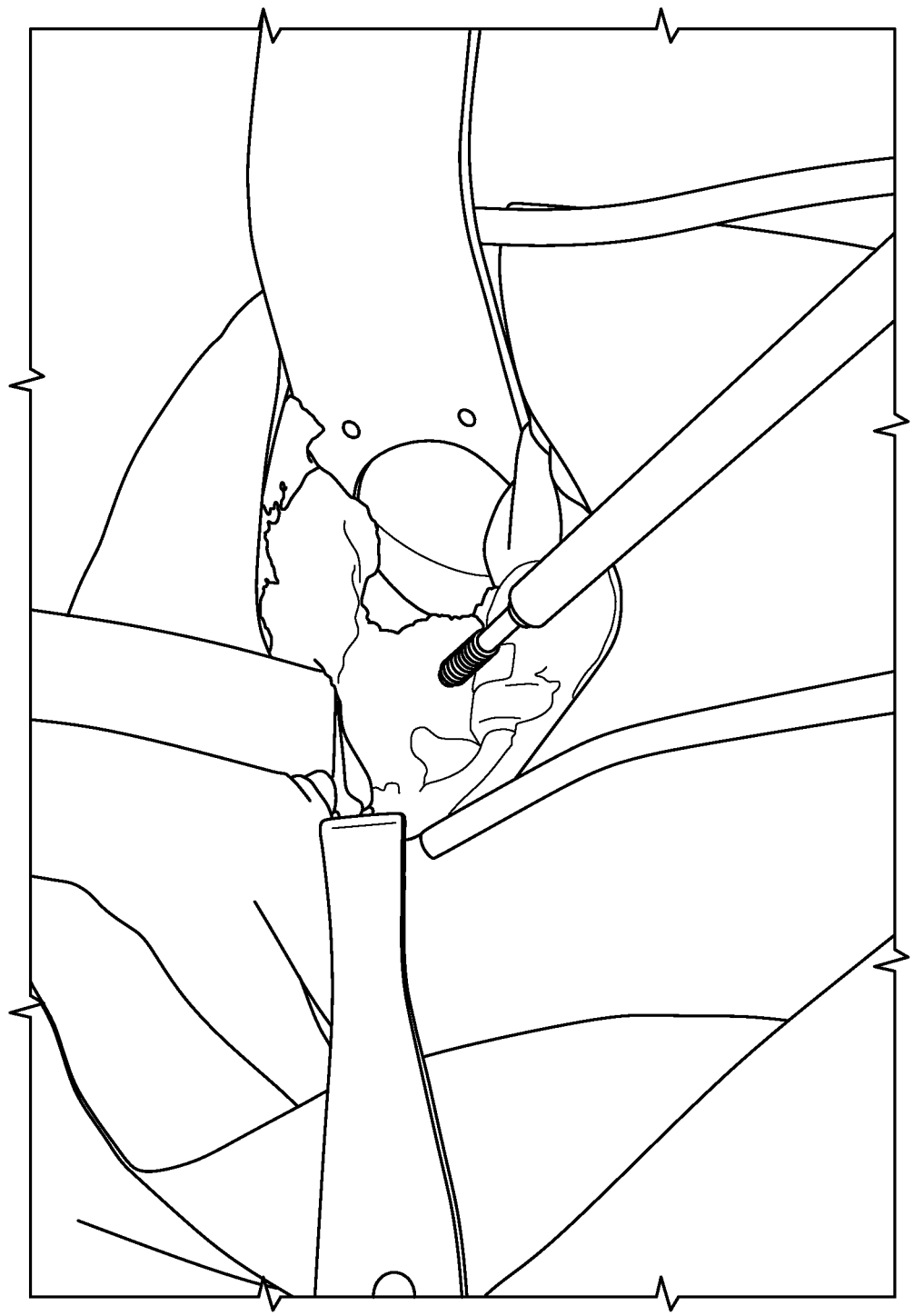
FIG. 15 illustrates fixation of the resected coracoid process of FIG. 5 to the glenoid via the screw of FIG. 14 in an embodiment of an open Latarjet procedure.
Figure 16:
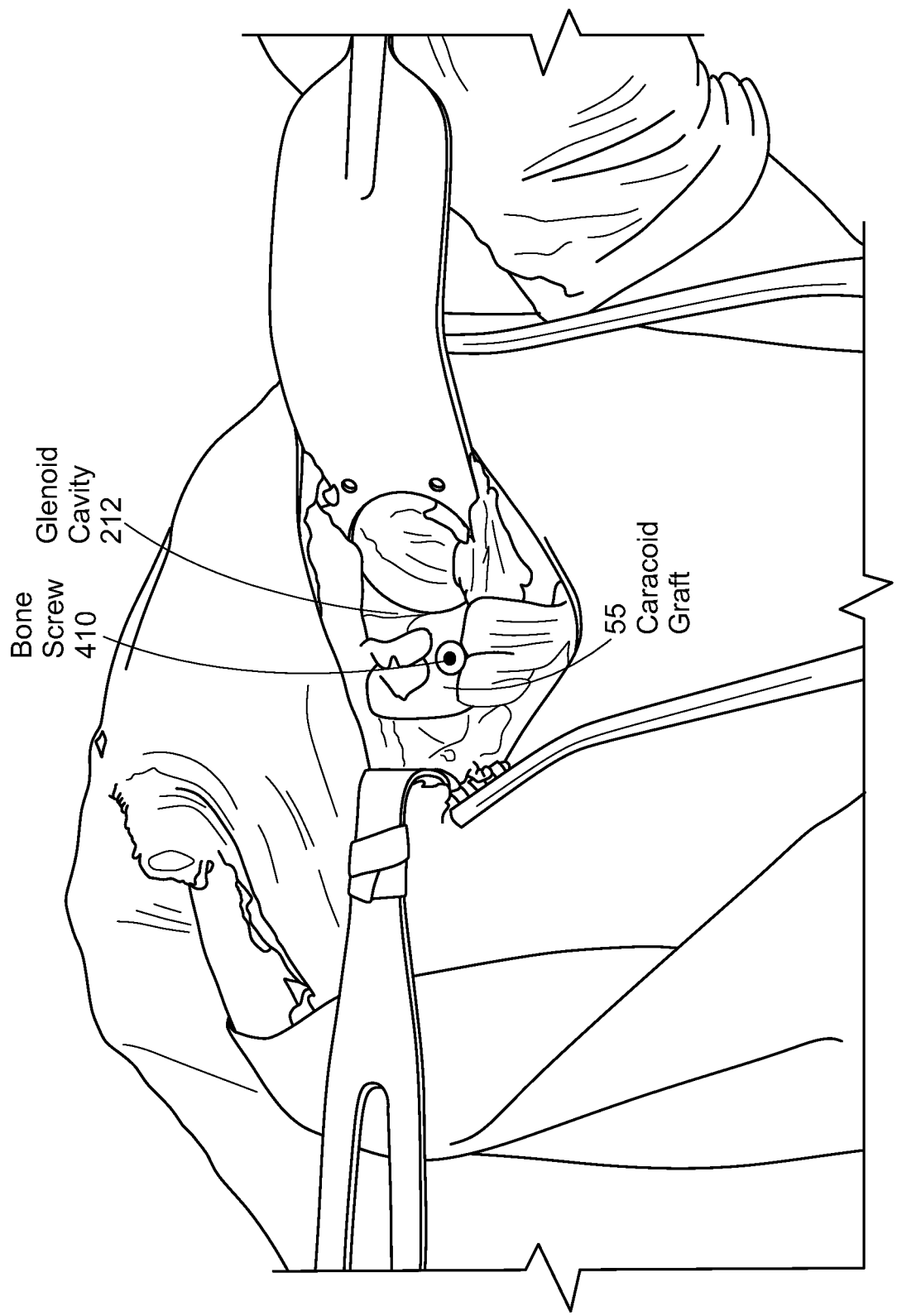
FIG. 16 illustrates adjustment of the coracoid process of FIG. 15 in an embodiment of an open Latarjet procedure.

FIGS. 14-20 illustrate mounting of the coracoid graft surface of the resected coracoid graft 55 to the glenoid graft surface. As illustrated in FIG. 14, using a driver 400 a screw 410 having threaded and non-threaded portions is inserted into the coracoid hole intended to align with the drilled glenoid hole (e.g., the hole closest to the coracoid tip). An embodiment of the screw and driver is discussed in greater detail with respect to U.S. patent application Ser. No. 13/439,099, entitled "BONE SCREW AND SELF RETAINING DRIVER," the entirety of which is incorporated by reference. FIGS. 15-16 illustrate mounting the coracoid to the glenoid at the inferior hole using the bone screw. In alternative embodiments, other mechanisms may be employed for fixation of the coracoid graft to the glenoid. Examples include, but are not limited to, endobuttons, sutures, anchors, and combinations thereof. Such examples are discussed in greater detail in U.S. Pat. No. 8,926,661, entitled "SURGICAL FASTENING," the entirety of which is incorporated by reference in its entirety.

Figure 17:
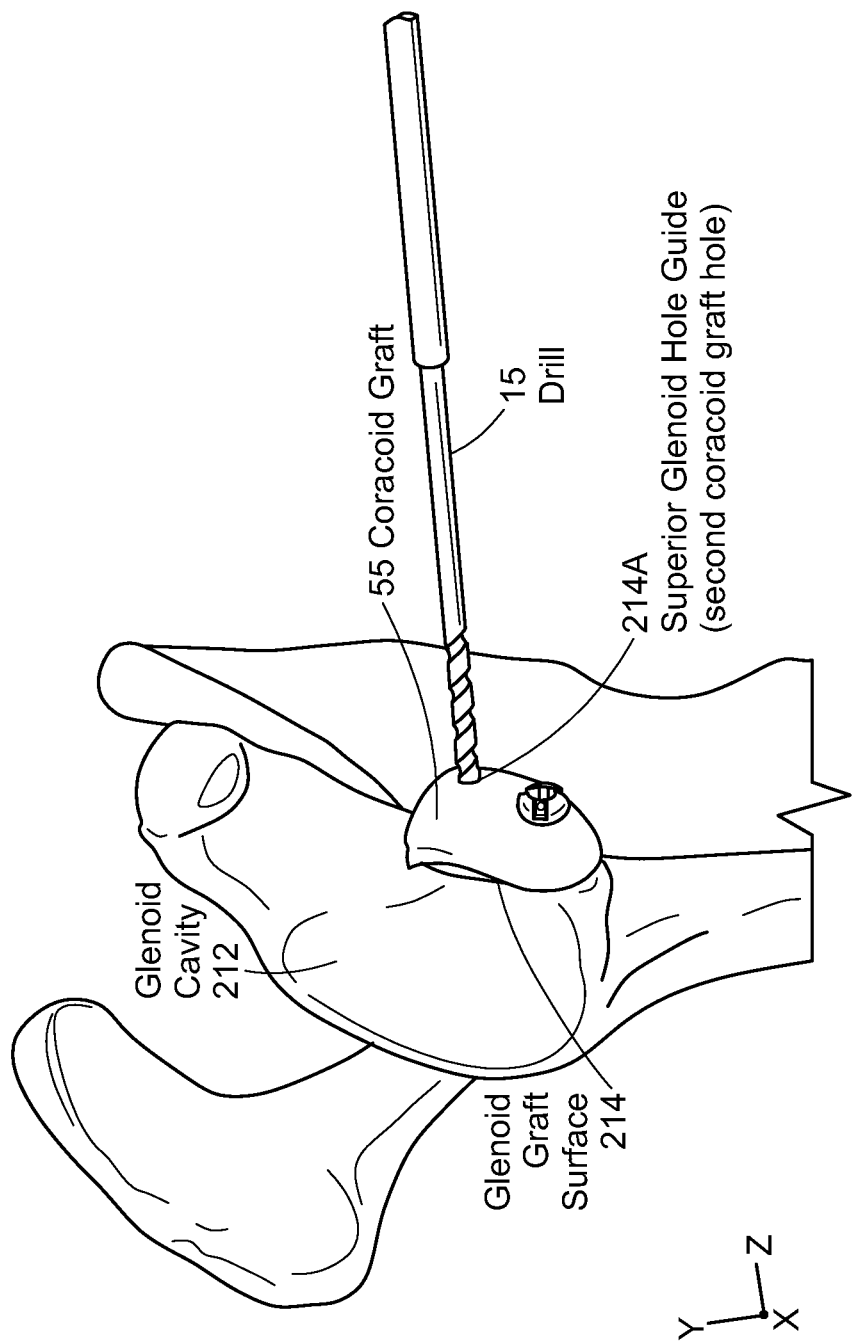
FIG. 17 is a schematic illustration demonstrating formation of a superior glenoid hole employing the coracoid process as a drill guide in an embodiment of an open Latarjet procedure.
Figure 18:
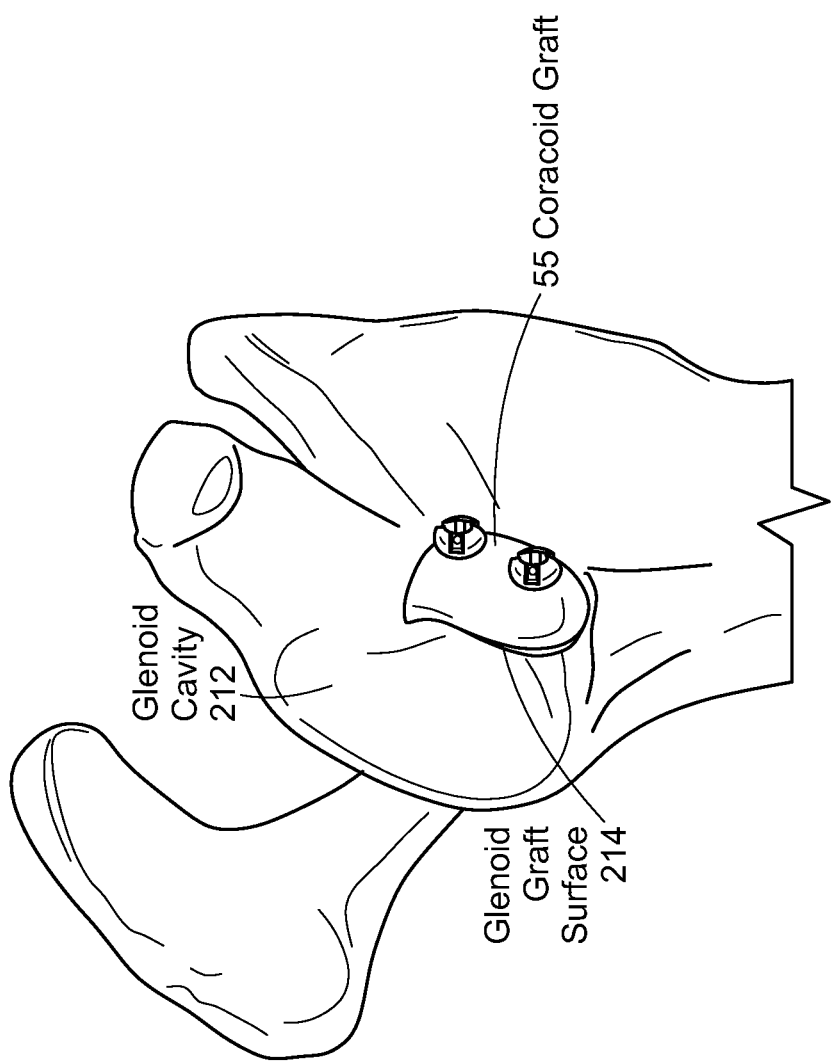
FIG. 18 is a schematic illustration of superior fixation of the coracoid process to the glenoid in an embodiment of an open Latarjet procedure.
Figure 19:
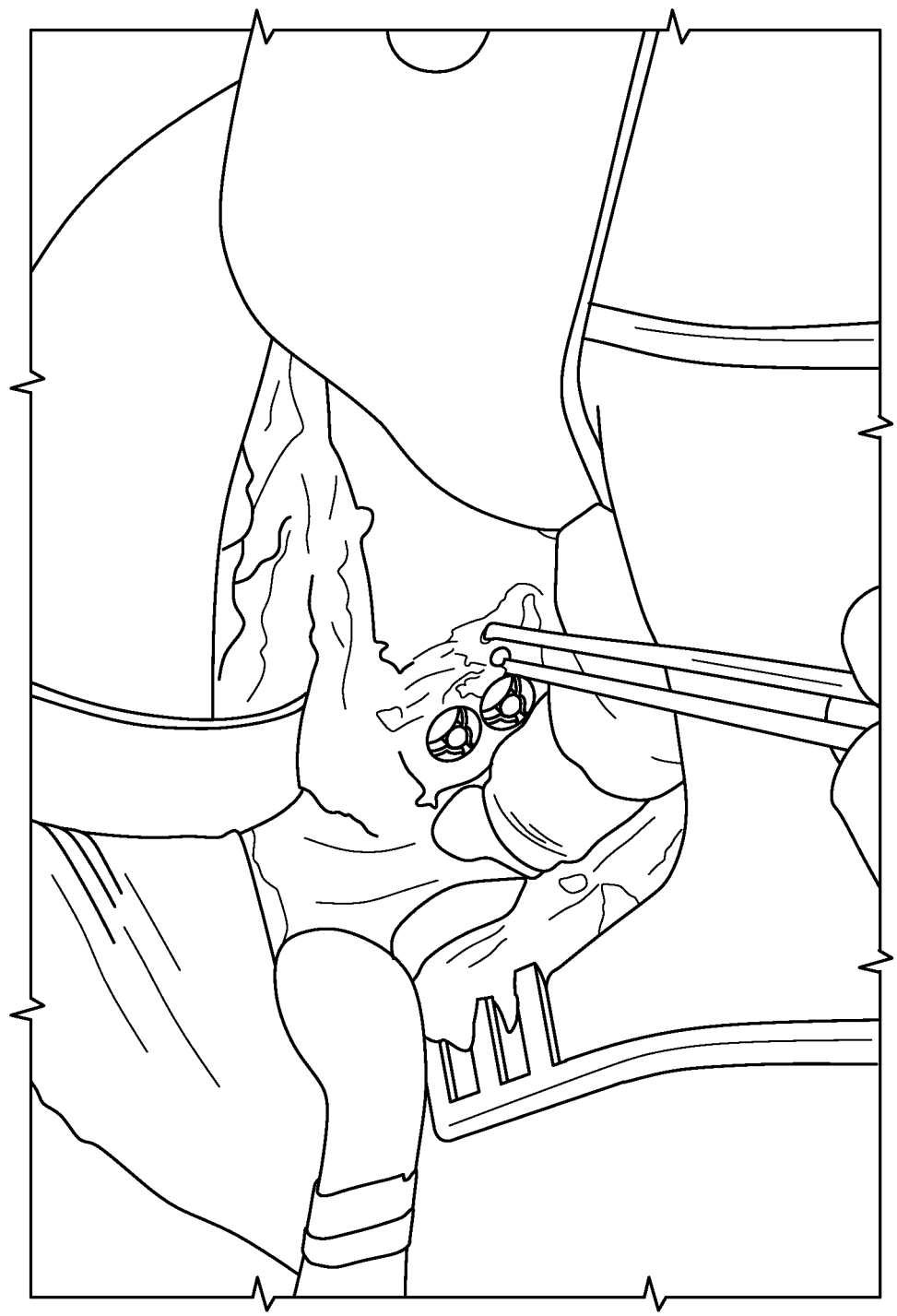
FIG. 19 illustrates a CA stump in an embodiment of an open Latarjet procedure.
Figure 20:
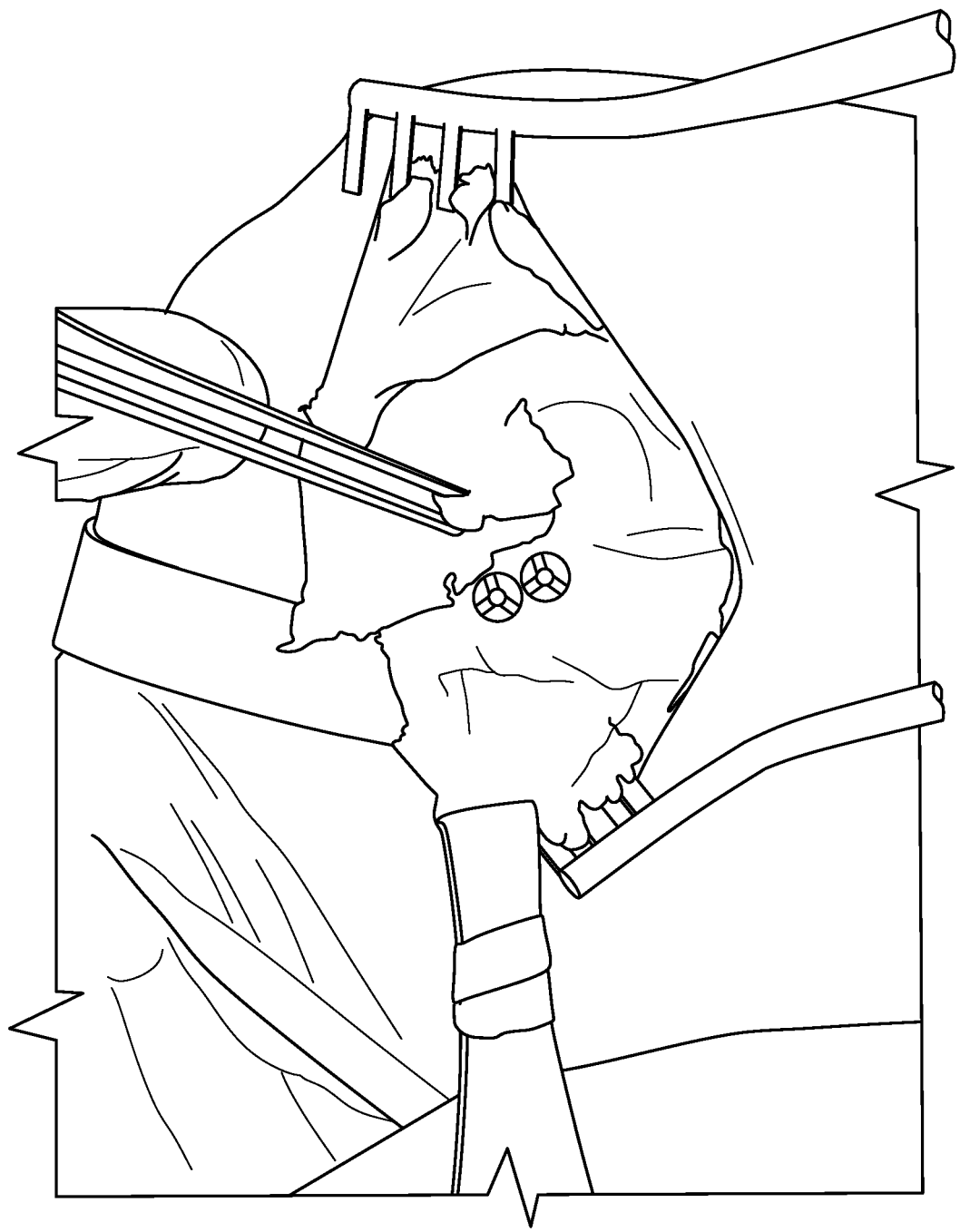
FIG. 20 illustrates capsule closure in an embodiment of an open Latarjet procedure.

FIGS. 17-20 illustrates fixation of the coracoid graft 55 to the glenoid graft surface 214 at a superior glenoid hole 214A in embodiments of the disclosure. With respect to FIG. 17, formation of the superior glenoid hole 214A is illustrated. As discussed above, a significant concern in Latarjet repair is ensuring that a sufficient amount of the glenoid surface and the coracoid graft surface are in contact under an appropriate level of pressure in order to promote successful bone fusion. In order to address this issue, the coracoid is "lightly" or provisionally secured via a first coracoid graft hole 152 or 154 to the glenoid by the bone screw at an inferior glenoid hole (as illustrated in FIG. 17), allowing the coracoid graft 55 to be rotated with respect to the glenoid graft surface 214. The coracoid graft 55 is positioned such that the unsecured coracoid graft hole 152 or 154 overlies a selected position on the glenoid graft surface 214. For example, the coracoid graft 55 is rotated such that the lateral edge of the coracoid nearest to the glenoid cavity surface 212 is approximately flush therewith. Subsequently, (as also illustrated in FIG. 17) the unsecured coracoid graft hole 152 or 154 is employed as a guide for drilling a superior glenoid hole, e.g., using drill 15. FIGS. 18-20 illustrate fixation of the unsecured (e.g., distal) end of the coracoid graft 55 to the glenoid at the superior glenoid hole 214A using a second bone screw (as described herein). In alternative embodiments, other mechanisms may be employed for fixation of the coracoid graft 55 to the glenoid. Examples include, but are not limited to, endobuttons, sutures, anchors, and combinations thereof.

The terms comprise, include, and/or plural forms of each are open ended and include the listed parts and can include additional parts that are not listed. The term and/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method of joint repair, comprising:
   forming a planar surface on a bone graft;
   forming a proximal hole and a distal hole through the bone graft, the proximal and distal holes oriented perpendicular to the planar surface of the bone graft, wherein the proximal hole is positioned closer to a cut end of the bone graft than the distal hole;
   forming a first hole in a patient's glenoid;
   securing the bone graft to the patient's glenoid at the first glenoid hole by a first fastener extending through the distal bone graft hole and the first glenoid hole;
   rotating the bone graft about the first fastener to orient the proximal bone graft hole to overlie the patient's glenoid;
   inserting a bone removal tool through the proximal bone graft hole after said rotation; and
   securing the bone graft to the patient's glenoid at the proximal bone graft hole by a second fastener extending through the proximal bone graft hole.

2. The method of claim 1, wherein the first glenoid hole is not formed concurrently with either the proximal or distal bone graft hole.

3. The method of claim 1, wherein the bone graft is a resected coracoid.

4. The method of claim 1, further comprising forming a second hole in the patient's glenoid by the bone removal tool, wherein the second glenoid hole is superior to the first glenoid hole and wherein the superior glenoid hole is formed after the inferior glenoid hole.

5. The method of claim 4, wherein the inferior and superior glenoid holes are formed at a selected angle and lateral offset with respect to an articular surface of the glenoid.

6. The method of claim 5, wherein the selected angle is chosen within the range between 5 degrees to 45 degrees.

7. The method of claim 5, wherein the selected angle is 10 degrees.

8. The method of claim 5, wherein the selected lateral offset is chosen within the range between 5 mm to 8 mm.

9. The method of claim 1, wherein forming the proximal hole and the distal hole through the bone graft comprises forming the proximal hole and the distal hole with a resection guide, the resection guide comprising:
   a gripping tool, comprising:
      a first handle portion and a second handle portion;
      a pivotably actuatable jaw including a first jaw portion at a distal end of the first handle portion, the first jaw portion extending from a first proximal end to a first distal end, and a second jaw portion at a distal end of the second handle portion, the second jaw portion extending from a second proximal end and to a second distal end; the first jaw portion comprising a first planar gripping surface extending from the first proximal end to the first distal end, and a first planar side surface extending from the first proximal end to the first distal end perpendicular to the first planar gripping surface; and the second jaw portion comprising a second planar gripping surface extending from the second proximal end to the second distal end, and a second planar side surface extending from the second proximal end to the second distal end perpendicular to the second planar gripping surface; and
      a pivot mounting the first jaw portion to the second jaw portion such that: the first and second planar gripping surfaces face one another and define a gripping area there-between, the gripping area dimensioned for and configured to receive a coracoid process;
   the first planar side surface and the second planar side surface lying in a same plane; and
   a tool axis extends through the pivot and the gripping area; and
      an alignment guide comprising an elongated guide body extending between a first end and a second end along a guide axis;
      wherein the alignment guide comprises at least three guide holes extending through a thickness of the elongated guide body, the at least three guide holes positioned along the guide axis and distanced apart, and wherein the at least three guide holes extend perpendicular to a plane of the first and second planar side surfaces of the jaw; and wherein the alignment guide is mounted to the gripping tool pivot adjacent the first end of the elongated guide body such that the alignment guide is rotatable about the pivot between the tool axis and a selected angle, and the alignment guide is capable of linear translation along the guide axis.

10. The method of claim 9, wherein the resection guide further includes a locking knob for securing the alignment guide at a selected location with respect to the gripping tool.

11. The method of claim 9, wherein the at least three guide holes extend through a boss extending from a surface of the elongated guide body opposite the jaw.

12. The method of claim 9, wherein forming the proximal hole through the bone graft comprises forming the proximal hole aligned with one of the at least three guide holes of the alignment guide.

13. The method of claim 12, wherein forming the distal hole through the bone graft comprises forming the distal hole aligned with another one of the at least three guide holes of the alignment guide.

14. The method of claim 1, further comprising measuring an offset distance between the distal hole and a lateral edge of the bone graft with an offset measurement tool.

15. The method of claim 14, wherein the measurement tool comprises an elongated shaft and a gauge at a distal end of the shaft, the gauge including a distally extending prong and a plurality of laterally extending fingers proximal to the distally extending prong, wherein each of the plurality of laterally extending fingers corresponds to a different known length.

16. The method of claim 15, wherein each of the plurality of laterally extending fingers is configured to correspond with a different glenoid drill guide.

17. The method of claim 15, further comprising:
inserting the prong into the distal hole;
rotating the measurement tool to compare a relative length of each of the fingers to the lateral edge;
identifying a representative laterally extending finger which is closest to the offset distance between the distal hole and the lateral edge; and
selecting a glenoid drill guide which corresponds with the identified representative finger.

18. The method of claim 17, wherein the glenoid drill guide includes an elongated tubular guide body having an internal lumen extending along a longitudinal axis thereof; and an offset paddle mounted at a distal end of the guide at an offset lateral distance from the tubular guide body and extending along a paddle axis, wherein the offset lateral distance correlates to the known length of the identified representative finger.

19. The method of claim 18, wherein the paddle axis is at an offset angle relative to the longitudinal axis of the tubular guide body.

20. The method of claim 1, wherein forming the planar surface on the bone graft comprises forming the planar surface with a rasp.

* * * * *